United States Patent [19]
Koch et al.

[11] Patent Number: 5,550,152
[45] Date of Patent: Aug. 27, 1996

[54] BENZOPYRAN AND RELATED LTB$_4$ ANTAGONISTS

[75] Inventors: Kevin Koch, Mystic; Lawrence S. Melvin, Jr., Ledyard; Lawrence A. Reiter, Mystic; Sally G. Ruggeri, Madison, all of Conn.

[73] Assignee: Pfizer Inc., New York, N.Y.

[21] Appl. No.: 256,809

[22] PCT Filed: Oct. 13, 1992

[86] PCT No.: PCT/US92/08555

§ 371 Date: Sep. 30, 1994

§ 102(e) Date: Sep. 30, 1994

[87] PCT Pub. No.: WO93/15066

PCT Pub. Date: Aug. 5, 1993

Related U.S. Application Data

[63] Continuation-in-part of Ser. No. 890,055, May 28, 1992, abandoned, which is a continuation of Ser. No. 824,678, Jan. 23, 1992, abandoned.

[51] Int. Cl.$^6$ .......................... A61K 31/35; C07D 311/22
[52] U.S. Cl. .......................... 514/458; 549/399; 549/400; 549/401; 549/403
[58] Field of Search .................................. 549/399, 400, 549/401, 403; 514/458

[56] References Cited

U.S. PATENT DOCUMENTS

| 4,565,882 | 1/1986 | Miyano et al. | 549/399 |
| 5,059,609 | 10/1991 | Eggler et al. | 514/314 |

FOREIGN PATENT DOCUMENTS

| 276064 | 11/1988 | European Pat. Off. . |
| 292977 | 11/1988 | European Pat. Off. . |
| 0404440 | 12/1990 | European Pat. Off. . |

OTHER PUBLICATIONS

Djurio et al. Journal of Medicinal Chemistry, vol. 32, pp. 1146–1147 (1989).

M. Uemura et al., in Tetrahedron Letters, vol. 21, No. 21, pp. 2069–2072 (1980).

*Primary Examiner*—Johann Richter
*Assistant Examiner*—John Peabody
*Attorney, Agent, or Firm*—Peter C. Richardson; Paul H. Ginsburg; Gezina Holtrust

[57] ABSTRACT

The invention relates to benzopyran leukotriene B$_4$ (LTB$_4$) antagonists and pharmaceutical compositions containing the compounds. The compounds inhibit the action of LTB$_4$ and are therefore useful in the treatment of LTB$_4$ induced illnesses such as inflammatory disorders.

10 Claims, No Drawings

BENZOPYRAN AND RELATED LTB$_4$ ANTAGONISTS

The instant application is a 371 of PCT/US92/085555, filed Oct. 13, 1992, which is a continuation-in-part of application Ser. No. 07/890,055, filed May 28, 1992, now abandoned, which is a continuation of application Ser. No. 07/824,678, file Jan. 23, 1992, now abandoned.

BACKGROUND OF THE INVENTION

This invention relates to novel benzopyran and other benzo-fused leukotriene B$_4$ (LTB$_4$) antagonists, to pharmaceutical compositions containing such compounds, and to a method of using such compounds as LTB$_4$ antagonists.

The compounds of this invention inhibit the action of LTB$_4$ and are therefore useful in the treatment of LTB$_4$ induced illnesses such as inflammatory disorders including rheumatoid arthritis, osteoarthritis, inflammatory bowel disease, psoriasis and other skin disorders such as eczema, erythma, pruritis and ache, stroke and other forms of reperfusion injury, graft rejection, autoimmune diseases, asthma, and other conditions where marked neutrophil infiltration occurs.

Leukotriene B$_4$ antagonists are disclosed in European patent publications 276 064 and 292 977 which refer to diphenylethers, benzophenones, and other compounds containing two phenyl groups, and 7-(3-alkoxy-4-alkanoylphenoxy)alkoxy benzopyran derivatives, respectively.

SUMMARY OF THE INVENTION

According to the invention, it was found that the following compounds of formula I have LTB$_4$ antagonistic properties:

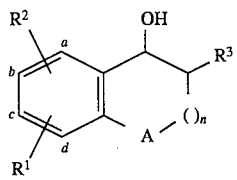

wherein A is O, CH$_2$, S, NH, or N(C$_1$-C$_6$ alkyl); n is 0, 1 or 2; R$^1$ is a substituent at position b or c as follows: carboxy; cis or trans —(CH$_2$)$_m$—CR$^4$=CR$^5$—CO$_2$H;

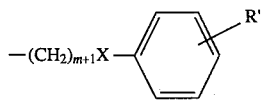

wherein m is 0, 1 or 2, R' is carboxy, tetrazolyl or CH$_2$OH, and X is O, CH$_2$, S, NH or N(C$_1$-C$_6$ alkyl); —(CH$_2$)$_m$CR$^4$R$^5$R$^6$ wherein m is as defined above; R$^4$ and R$^5$ are hydrogen or each independently are C$_1$-C$_6$ alkyl, or are taken together with the carbons to which they are attached to form C$_3$-C$_7$ cycloalkyl, R$^6$ is hydroxyl, carboxy, or tetrazolyl; or —CONR$^7$R$^8$ wherein R$^7$ and R$^8$ are hydrogen or each independently are C$_1$-C$_6$ alkyl, C$_1$-C$_4$ perfluoroalkyl, C$_1$-C$_6$ alkylsulfinyl, phenylsulfinyl, C$_1$-C$_6$ alkylsulfonyl, phenylsulfonyl, R$^9$-substituted phenyl or hydroxy, except that R$^7$ and R$^8$ cannot be both hydroxy; R$^2$, R$^9$, R$^{15}$, and R$^{16}$ are hydrogen or each independently are one or any two of the following: fluoro, chloro, C$_1$-C$_6$ alkyl, C$_1$-C$_6$ alkoxy, C$_1$-C$_4$ perfluoroalkyl, C$_1$-C$_4$ perfluoroalkoxy, C$_1$-C$_6$ alkylthio, C$_1$-C$_6$ alkylsulfinyl or C$_1$-C$_6$ alkylsulfonyl; R$^3$ is —(CH$_2$)$_q$CHR$^{11}$R$^{12}$, —O(CH$_2$)$_q$R$^{12}$, —O(CH$_2$)$_p$CHR$^{11}$R$^{12}$, or —O(CH$_2$)$_p$R$^{12}$, wherein p is 0, 1 or 2 and q is 0, 1, 2, or 3; R$^{11}$ is hydrogen, C$_1$-C$_6$ alkyl or R$^{16}$-substituted phenyl wherein R$^{16}$ is as defined above; R$^{12}$ is C$_1$-C$_6$ alkyl or C$_3$-C$_8$ cycloalkyl; or phenyl, thienyl, pyridyl, furyl, naphthyl, quinolyl, isoquinolyl, pyrimidinyl, or pyrazinyl, each of which is optionally substituted by phenyl, R$^5$, or R$^{15}$-substituted phenyl wherein R$^{15}$ is as defined above; and the salts and esters of those compounds of formula I containing a carboxy group, wherein the esters contain an ester group R$^{13}$ selected from the group consisting of C$_1$-C$_6$ alkyl, phenyl(C$_1$-C$_6$) alkyl, C$_3$-C$_7$ cycloalkyl, and benzyl substituted by fluoro, chloro, C$_1$-C$_6$ alkyl or C$_1$-C$_6$ alkoxy.

Preferred compounds of the invention are those of formula I wherein A is oxygen, those wherein n is 1, those wherein R$^1$ is at position c and is 1-carboxyethyl, 2-carboxy-2-propyl, 1-carboxypropyl, 3-carboxy-3-pentyl, 1-carboxycyclopentyl, 1-carboxycyclohexyl or 1-(5-tetrazoyl)cyclopentyl, those wherein R$^2$ is hydrogen or monofluoro, and those wherein R$^3$ is benzyl, 4-fluorobenzyl, 4-phenylbenzyl or 4-(4-fluorophenyl)benzyl. Specific compounds of the formula I are those wherein A is oxygen, n is 1, R$^1$ is a substituent at position c and is 1-carboxyethyl, 2-carboxy-2-propyl, 1-carboxypropyl, 3-carboxy-3-pentyl, 1-carboxycyclopentyl, 1-carboxycyclohexyl or 1-(5-tetrazolyl)cyclopentyl, R$^2$ is hydrogen or monofluoro, and R$^3$ is benzyl, 4-fluorobenzyl, 4-phenylbenzyl, 4-(4-fluorophenyl)benzyl, phenethyl or phenoxy.

More specific compounds of the formula I are those wherein n is 1, A is O, R$^1$ is 1-carboxycyclopentyl at position c, R$^2$ is hydrogen, R$^3$ is benzyl or 4-phenylbenzyl, and R$^3$ and the adjacent hydroxy group are trans. Other specific compounds of the formula I are those wherein R$^3$ is benzyl and R$^1$ is carboxyethyl, 2-carboxypropyl, 1-carboxypropyl, 3-carboxy-3-pentyl, 1-carboxycyclohexyl, or 1-(5-tetrazolyl)cyclopentyl, those wherein R$^3$ is benzyl, R$^2$ is monofluoro at position a, R$^1$ is 1-carboxycyclopentyl, and R$^3$ and the adjacent hydroxy group are trans, and those wherein R$^3$ is phenethyl, R$^2$ is hydrogen, R$^1$ is 1-carboxycyclopentyl, and R$^3$ and the adjacent hydroxy group are cis.

The present invention also relates to a pharmaceutical composition for the treatment of LTB$_4$ induced illnesses comprising a compound of the formula I as defined above in an amount effective in the treatment of LTB$_4$ induced illnesses, and a pharmaceutically acceptable carrier. Preferred compositions are those wherein the compound of formula I is a preferred compound.

This invention further comprises a method for the receptor binding inhibition of LTB$_4$ by administering to a subject in need of such inhibition a compound of formula I as defined above.

The invention further includes a process for the preparation of a compound of the formula

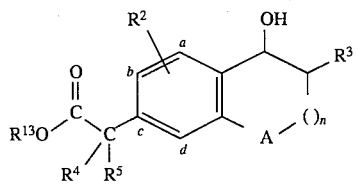

wherein A is O, CH$_2$, S, NH or N(C$_1$-C$_6$)alkyl); n is 0, 1 or 2; R$^2$ R$^9$, R$^{15}$ and R$^{16}$ are hydrogen or each independently are one or any two of the following: fluoro, chloro, bromo, C$_1$-C$_6$ alkyl, C$_1$-C$_6$ alkoxy, C$_1$-C$_4$ perfluoroalkyl, C$_1$-C$_4$ perfluoroalkoxy, C$_1$-C$_6$ alkylthio, C$_1$-C$_6$ alkylsulfinyl, or C$_1$-C6 alkylsulfonyl, R$^3$ is (CH$_2$)$_q$CHR$^{11}$R$^{12}$, —(CH$_2$)$_q$R$^{12}$, —O(CH$_2$)$_p$CHR$^{11}$R$^{12}$, or —(CH$_2$)$_p$R$^{12}$, wherein p is 0, 1 or 2 and q is 0, 1, 2, or 3; $R^4$ and $R^5$ are hydrogen or each independently are $C_1$-$C_6$ alkyl or are taken together with the carbons to which they are attached to form $C_3$-$C_7$ cycloalkyl; $R^{11}$ is hydrogen, $C_1$-$C_6$ alkyl or $R^{16}$-substituted phenyl wherein $R^{16}$ is as defined above; $R^{12}$ is $C_1$-$C_6$ alkyl or $C_3$-$C_8$ cycloalkyl; or phenyl, thienyl, pyridyl, furyl, naphthyl, quinolyl, isoquinolyl, pyrimidinyl, or pyrazinyl, each of which is optionally substituted by phenyl, $R^{15}$, or $R^{15}$-substituted phenyl wherein $R^{15}$ is as defined above; and $R^{13}$ is $C_1$-$C_6$ alkyl, phenyl($C_1$-$C_6$) alkyl, cycloalkyl or benzyl substituted by fluoro, chloro, $C_1$-$C_6$ alkyl, or $C_1$-$C_6$ alkoxy, which comprises reacting a compound of the formula

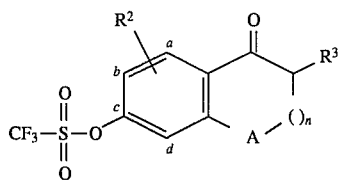

wherein A, n, $R^2$ and $R^3$ are as defined above, with a trimethylsilyl ketene-acetal of the formula

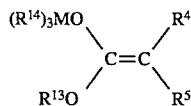

wherein $R^4$, $R^5$, and $R^{13}$ are as defined above, $R^{14}$ is $C_1$-$C_6$ alkyl or phenyl, and M is Si or Zn, and reducing the compound formed.

The invention also includes a compound of the above formula III wherein $R^2$, $R^9$, $R^{15}$ and $R^{16}$ are hydrogen or each independently are one or any two of the following: fluoro, chloro, $C_1$-$C_6$ alkyl, $C_1$-$C_6$ alkoxy, $C_1$-$C_4$ perfluoralkyl, $C_1$-$C_4$ perfluoroalkoxy, $C_1$-$C_6$ alkylthio, $C_1$-$C_6$ alkylsulfinyl or $C_1$-$C_6$ alkylsulfonyl; $R^3$ is —$(CH_2)_q CHR^{11}R^{12}$, —$(CH_2)_q R^{12}$, —$O(CH_2)_p CHR^{11}R^{12}$, or —$O(CH_2)_p R^{12}$, wherein p is 0, 1 or 2 and q is 0, 1, 2, or 3; $R^4$ and $R^5$ are hydrogen or each independently are $C_1$-$C_6$ alkyl or are taken together with the carbons to which they are attached to form $C_3$-$C_7$ cycloalkyl; $R^{11}$ is hydrogen, $C_1$-$C_6$ alkyl or $R^{16}$-substituted phenyl wherein $R^{16}$ is as defined above; and $R^{12}$ is $C_1$-$C_6$ alkyl or $C_3$-$C_8$ cycloalkyl; or phenyl, thienyl, pyridyl, furyl, naphthyl, quinolyl, isoquinolyl, pyridinyl, or pyrazinyl, each of which is optionally substituted by phenyl, $R^{15}$, or $R^{15}$-substituted phenyl wherein $R^{15}$ is as defined above.

The term "$C_1$-$C_6$ alkyl" whenever used in the disclosure herein such as in the definitions of $R^1$ to $R^{14}$ denotes saturated monovalent straight or branched aliphatic hydrocarbon radicals having one to six carbon atoms, such as methyl, ethyl, propyl, t-butyl, hexyl, etc. Similarly, the terms $C_3$-$C_7$ cycloalkyl and $C_3$-$C_8$ cycloalkyl denote a cycloalkyl group having from three to seven or eight carbon atoms, respectively, such as cyclopropyl, cyclohexyl, cyclooctyl, etc.

When A is oxygen and n is 1 in a compound of formula I, the compound may be described either as a 3,4-dihydrobenzopyran or a chromane.

The compounds of the invention have two asymmetric carbon atoms indicated by asterisks in the following formula:

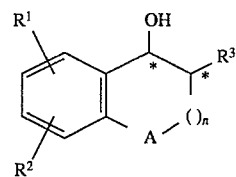

The stereoisomers may be designated with reference to R and S rotation in accordance with standard nomenclature. When reference is made herein to S,R, or R,S, a single enantiomerically pure compound is meant, whereas S*, R* and R*, S* denote a racemic mixture. The invention includes the racemic mixtures and optical isomers of formula I.

DETAILED DESCRIPTION OF THE INVENTION

According to a specific method of the invention, compounds of above formula II, which are more specific compounds of formula I, wherein $R^1$ is —$(CH_2)_m CR^4R^5R^6$, m is 0 and $R^6$ is carboxy or the esters thereof are prepared by reacting compounds of above formulae III and IV to form a compound of the formula V (not shown) followed by reduction to form the compound of formula I.

The reaction of compounds III and IV is generally conducted in a solvent. Suitable solvents are ether solvents such as tetrahydrofuran, diethyl ether, ethylene glycol dimethyl ether and 1,4-dioxane, dipolar aprotic solvents such as dimethylformamide, N,N-dimethylacetamide, acetonitrile, dimethyl sulfoxide, hexamethylphosphoramide, N,N-dimethylpropylene urea, non-polar aromatic solvents such as xylene, benzene, chlorobenzene and toluene, and halogenated solvents such as methylene chloride, chloroform and dichloroethane. Specific suitable solvents are xylene, or a mixture of equal volumes of ethylene glycol dimethylether and dimethyl formamide. The reaction temperature ranges from −78° C. to 200° C. depending on the boiling point of the solvent used and usually ranges from about 80° to about 150° C.

The reaction may be carried out in the presence of a Lewis acid such as zinc chloride, aluminum chloride, magnesium bromide, tin chloride and titanium chloride. When present, the amount of Lewis acid ranges from about 0.05 to about 2 equivalent per mole of compound III.

The reaction is generally carried out with a palladium catalyst. Suitable palladium catalysts are tetrakistriphenyl phosphine palladium, bis-benzonitrile palladium chloride, allyl palladium chloride dimer, palladium chloride, palladium acetate, palladium on carbon, and bisacetonitrile palladium chloride. A specific catalyst comprises 5% by weight allyl palladium chloride dimer or 5% by weight bisbenzonitrile palladium chloride. Generally, about 0.001 equivalent to one equivalent of catalyst per mole of substrate is used.

The reaction is generally carried out in the presence of a phosphine ligand such as triphenyl phosphine, tri-o-tolylphosphine and tri-2-furylphosphine in an amount of about 0.1 to about 5, preferably 1 to 2, molar equivalents per mole of substrate used.

The reduction of the compound of the formula V is carried out in a conventional manner with sodium borohydride in an alcohol solvent at ambient temperature to form the compound of formula I.

The compounds of formula III wherein $R^3$ is $(CH_2)_q CHR^{11}R^{12}$ or $(CH_2)_q R^{12}$ may be prepared according to reaction Scheme I from a compound of the formula VI wherein A, n and $R^2$ are as defined with reference to formula I.

SCHEME I

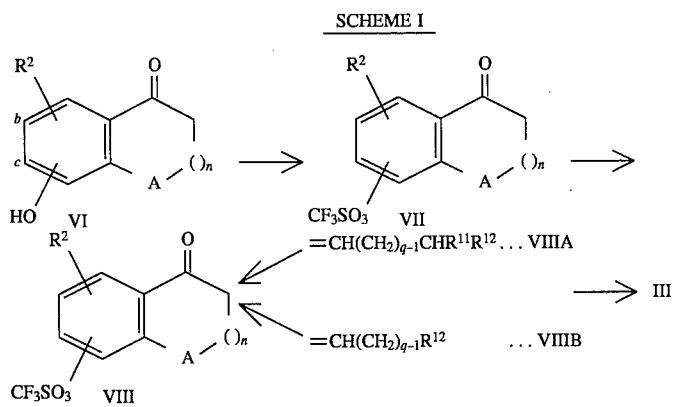

The compound of formula VI is reacted with trifluoromethane sulfonic anhydride (also called triflic anhydride) in a suitable solvent such as methylene chloride in the presence of triethylamine to form the compound of formula VII.

The group $R^3$ when defined as $-(CH_2)_q CHR^{11}R^{12}$ or $-(CH_2)_q R^{12}$ may be introduced into the compound of formula VII by a two step procedure comprising reacting with an aldehyde of the formula $R^{11}R^{12}CH(CH_2)_{q-1} CHO$ or $R^{12}(CH_2)_{q-1}CHO$ to form a compound of the formulae VIIIA or VIIIB, respectively, and then hydrogenating. The reaction with the aldehyde is conducted in the presence of a pyrrolidine catalyst or with hydrochloric acid catalyst in acetic acid. The hydrogenation is carried out with hydrogen and a palladium catalyst in a conventional manner.

The compounds of formula VI are generally commercially available. If not, they may be obtained by prior art methods. For instance, the compounds of formula VI wherein A is oxygen and n is 1 may be obtained from $R^2$-substituted 2',4'-dihydroxy-3-chloropropiophenone (hereafter compound 1) by cyclization with sodium hydroxide. Compound 1 may be prepared from $R^2$-substituted resorcinol and 3-chloropropionic acid in the presence of an acid, preferably trifluoromethane sulfonic acid. The compounds of formula VI wherein A is sulphur and n is 1 may similarly be obtained from $R^2$-substituted 4' or 5'-hydroxy-2'-sulfhydryl-3-chloropropiophenone which may be obtained from $R^2$-substituted 3-hydroxythiophenol.

The compounds of formula VI wherein n is 2 and A is O or S may similarly be obtained by reaction of $R^2$-substituted resorcinol or 3-hydroxythiophenol, respectively, and 4-chlorobutyric acid, and cyclization with sodium hydroxide.

The group $R^3$ when defined as $-O(CH_2)_p CHR^{11}R^{12}$ or $-O(CH_2)_p R^{12}$ may be introduced into the compound of formula VI and more generally into a compound of the formula IX by the procedure outlined in Scheme II. The compound of formula VI is the compound of formula IX wherein $R^1$ is $CF_3SO_3$.

SCHEME II

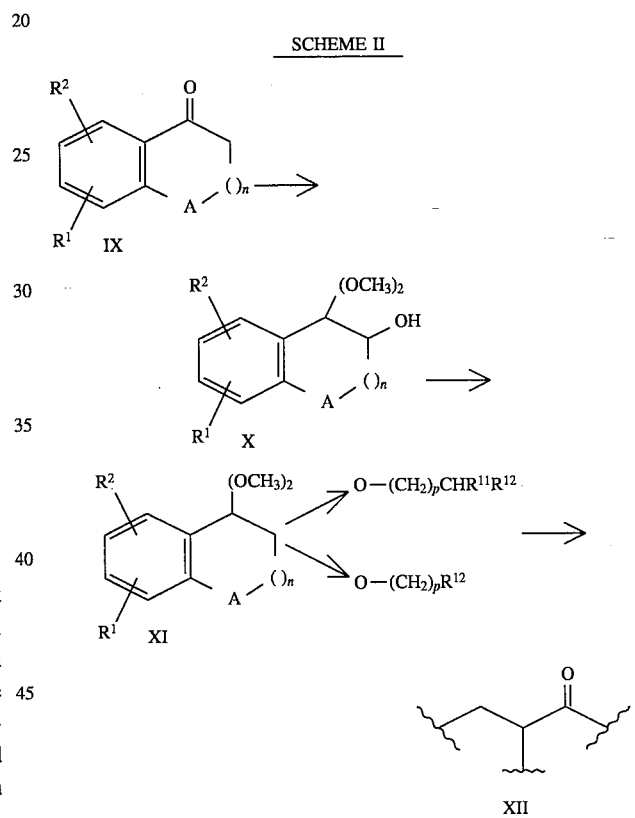

The compounds of formula IX may be prepared from compounds of formula XIII (hereafter) wherein $R^3$ is replaced by hydrogen, by reaction with $R^1I$ wherein $R^1$ is as defined with reference to Scheme III.

The compounds of formula X may be prepared from the compounds of formula IX by mixing thereof with 20% potassium hydroxide and adding phenyldiacetoxy iodide.

The compounds of formula X when combined with $Br(CH_2)_p CHR^{11}R^{12}$, or $Br(CH_2)_p R^{12}$, form compounds of the formula XI which are converted to compounds of the formula XII by hydrolysis with an acid such as hydrochloric acid. The compounds of formula XII on reduction, as described above for the reduction of the compound of formula V, form compounds of the formula I.

The compounds of formula III wherein $R^3$ is as defined with reference to formula I may be converted into compounds of formula I wherein $R^1$ is $(CH_2)_m CR^4 \!=\! CR^5\!-\!CO_2H$ in accordance with reaction Scheme III.

SCHEME III

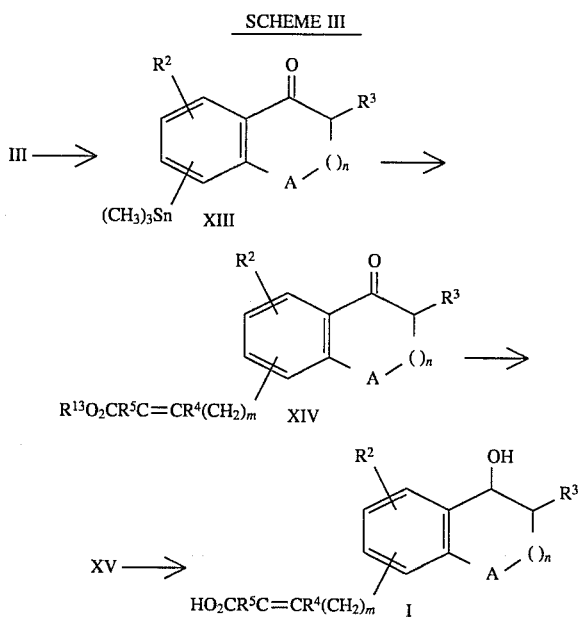

The compound of formula XIII is formed by reaction of the compound of formula III with $(CH_3)_3SnSn(CH_3)_3$ and a palladium catalyst such as tetrakistriphenyl phosphine palladium $(Pd(PPh_3)_4)$ in the presence of a phosphine ligand, as described above for the reaction of compounds of the formulas III and IV. The compound of formula XIII is converted to a compound of formula XIV by reaction with an ester-protected compound of the formula $R^{13}O_2CR^5C\!=\!CR^4\!-\!(CH_2)_mZ$ wherein $R^4$, $R^5$, $R^{13}$ and m are as defined with reference to formula I, and Z is iodo, bromo or $CF_3SO_3$. The coupling reaction proceeds in the presence of a palladium catalyst, such as bistriphenyl phosphine palladium chloride, as described above.

The ketone esters of the formula XIV are first reduced to the corresponding hydroxyl compounds XV (formula not shown) and then hydrolyzed to the corresponding acid of formula I. The reduction proceeds with sodium borohydride. Generally, the reduction is carried out in a solvent. Suitable solvents are lower alcohols having one to six carbon atoms, mixtures of lower alcohols with organic solvents such as tetrahydrofuran or dioxane, and mixtures of water-miscible lower alcohols or other water-miscible organic solvents with water. The solvent is preferably a lower alcohol such as methanol-or ethanol. The reaction temperature generally ranges from about −78° C. to about 100° C., and usually from about 0° C. to about 25° C.

The reduction step results in a stereoisomeric mixture of the ester compounds of formula I having the following structures:

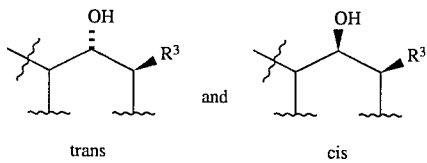

trans                cis

These cis and trans isomers may be separated by conventional column chromatography.

Resolution of the enantiomeric mixture resulting after separation of the cis and trans isomers may be accomplished by various methods. In one method, a compound of the formula I wherein $R^1$ contains a carboxyl group (COOH) is reacted with a chiral base such as ephedrine in a polar solvent such as ethyl acetate to form diastereomeric salts Which are separated and then converted into optically pure acids by treatment with an acid such as aqueous mineral acid, e.g. aqueous hydrogen chloride. In another method, a compound of the formula I wherein $R^1$ contains a carboxylic acid ester group is reacted with an optically active acid such as R-mandelic acid or N-t-butoxycarbonyl-D-tryptophan to form diastereomeric esters with the hydroxyl group which after separation are converted into optically pure acids by treatment with a base such as sodium hydroxide in methanol or ethanol. Removal of the resolving ester group and hydrolysis of the carboxylic acid ester group in $R^1$ is conveniently carried out with aqueous base such as an alkali metal hydroxide, e.g. sodium hydroxide, at temperatures ranging from about room temperature to the reflux or boiling temperature of the solvent or solvent mixture used. The reaction may be conducted in the presence of a co-solvent such as methanol, ethanol or tetrahydrofuran.

The compound of formula I wherein $R^1$ is carboxy and $R^2$ is hydrogen may be prepared from the intermediate compound of the formula III by first replacing the $CF_3SO_3\!-\!$ group by methoxycarbonyl, and then hydrolyzing. The replacement reaction proceeds with carbon monoxide in the presence of palladium acetate, 1,1′-bis(diphenylphosphine)ferrocene (DPPF), methanol and triethylamine.

The hydrolysis is as previously described with reference to Scheme III.

The compounds of formula I wherein $R^1$ is $-\!(CH_2)_mCR^4R^5R^6$ wherein m, $R^4$, $R^5$ and $R^6$ are as defined above with reference to formula I will be designated hereafter as compounds of the formula XXI (not shown). Although the following chemistry describes the preparation of compounds of formula XVI, wherein $R^1$ is $-\!(CH_2)_mCR^4R^5R^6$, particularly $R^1$ is $-\!(CH_2)_mCR^4R^5CO_2C_2H_5$, it is understood that the same chemistry applies to compounds of formula XVI having a different $R^1$, as defined with reference to formula I, which is inert under the reaction conditions specified below.

Formula XXI, $R^6$ is tetrazolyl

The title compounds may be prepared from a compound of the formula

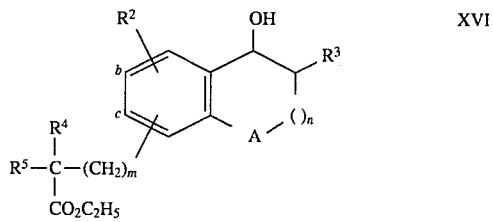

According to this method, the compound XVI is first reacted with t-butyldimethyl-silylchloride in the presence of imidazole and dimethylformamide to protect the hydroxyl group as known in the art. The protected compound is reacted with ammonia and triethylaluminum in xylene to replace the $-\!CO_2C_2H_5$ group by cyano. The cyano group is replaced by trimethylstannyl-tetrazolyl by reaction with trimethylstannylazide in toluene. Conversion to the tetrazolyl and removal of the silyl protecting group is accomplished by reaction with tetrabutylammonium fluoride in tetrahydrofuran.

The starting material of formula XVI is identical to the compound of above formula II wherein $R^{13}$ is ethyl and m is o, when the specific substituent $R^1$ in formula XVI is at position c. Preparation of this starting material is described above.

The starting material XVI when the specific substituent $R^1$ therein is at position b, m is 0, 1 or 2, n is 1, and A is O, S, NH or N($C_1$-$C_6$) alkyl has the formula XIX in reaction Scheme IV below, and may be prepared according to the procedure in reaction Scheme IV.

SCHEME IV

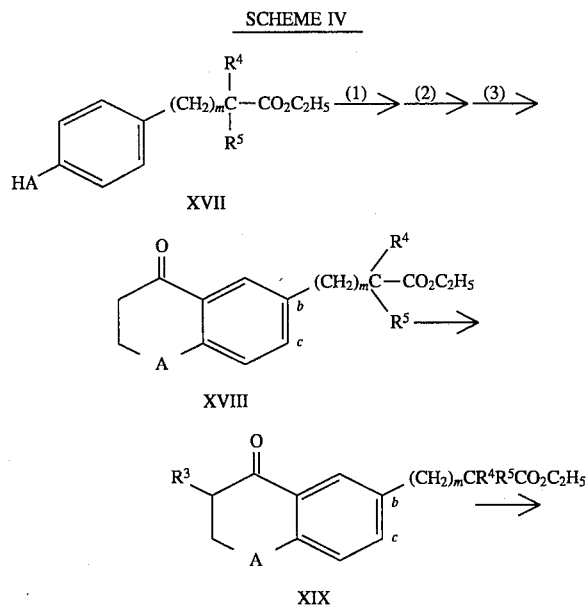

The compound of formula XVII is converted by subsequent reactions with (1) acrylonitrile, (2) hydrolysis with concentrated hydrochloride, and (3) cyclization with polyphosphoric acid to form the compound of formula XVIII. Introduction of group $R^3$ to form the compound of formula XIX is as described with reference to reaction Scheme I. The hydrogenation and hydrolysis of the compound of formula XIX is as described with reference to Scheme III in the conversion of compounds XIV to compound I.

The compound of formula XVII may be prepared from 3-hydroxyphenyl acetic acid by introduction of groups $R^4$ and $R^5$ by known methods, e.g. as illustrated in preparation Example 2 hereafter.

The starting material XVI when $R^1$ therein is at position b, m is 0, 1 or 2, n is 0 or 2 and A is O, S, NH, or N($C_1$-$C_6$) alkyl may be prepared by reacting the compound of formula XVII with $BrCH_2CN$ or $BrCH_2CH_2CH_2CN$ in step (1) of Scheme IV and converting further as described with reference to Scheme IV.

The starting material XVI wherein $R^1$ is at position b, A is $CH_2$, m is 0, 1 or 2, and n is 0, 1 or 2 may be prepared as shown in Scheme V.

SCHEME V

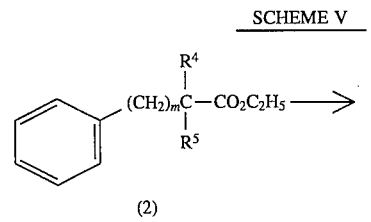

-continued
SCHEME V

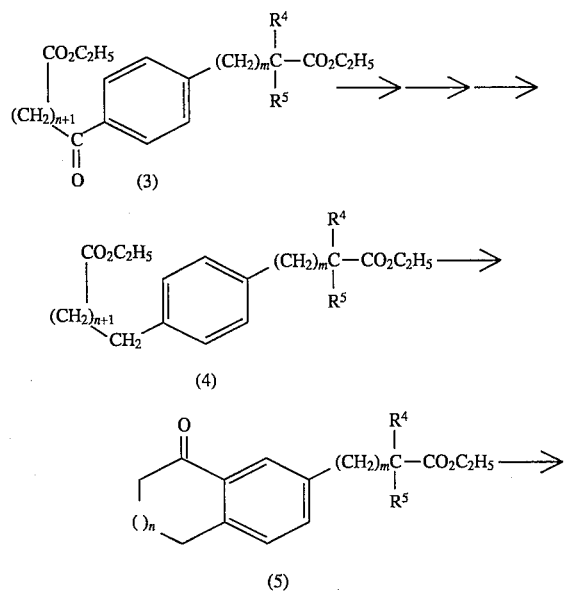

The benzene derivative (2) is reacted with a mono acid chloride mono ester of malonic, succinic or glutaric acid in the presence of a Friedel Crafts catalyst such as aluminum chloride. The ketone (3) is converted to the corresponding propylene dithiol with propylene dithiol and boron trifluoride catalyst. The formed compound is reduced with Raney nickel to compound (4). On saponification of compound (4) and using closure with polyphosporic acid, the bicyclic compound (5) is formed. Introduction of group $R^3$ is as described in Scheme I.

The starting material XVI when $R^1$ therein is at position c, n and A are as defined with reference to formula I, and m is 1 or 2, may be prepared in a similar manner as described above for compounds XVI wherein group $R^2$ is at position b.

Formula XXI, $R^6$ is $CO_2H$

The title compounds may be prepared by saponification of a compound of the formula I wherein $R^1$ is —$(CH_2)_m CR^4R^5CO_2CH_3$ the preparation of which is described above.

Formula XXI, $R^6$ is OH

The title compounds wherein m is 0, 1 or 2, and $R^4$ and $R^5$ are each hydrogen may be prepared by conventional lithium aluminum hydride hydrogenation of the compound of the formula I wherein $R^1$ is —$(CH_2)_m CO_2CH_3$, wherein m is 0, 1 or 2.

The title compounds wherein m is 0, 1 or 2, and $R^4$ and $R^5$ are each alkyl may be prepared by reacting the corresponding compounds wherein $R^4$ and $R^5$ are hydrogen with one equivalent of a Grignard reagent containing group $R^4$, e.g. $R^4$MgCl, followed by one equivalent of a Grignard reagent containing group $R^5$, e.g. $R^5$MgCl.

The title compounds wherein m is 0, 1 or 2, and $R^4$ and $R^5$ are taken together to form $C_3$-$C_7$ cycloalkyl are similarly prepared by reacting the corresponding compounds wherein $R^4$ and $R^5$ are hydrogen with a Grignard reagent derived from a $C_3$-$C_7$ dihalo alkane, e.g. ClMg($C_3$-$C_7$ alkanyl) MgCl.

The compounds of formula XXI wherein $R^4$ and $R^5$ are hydrogen, $R^6$ is

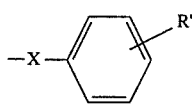

wherein R' is carboxy, tetrazolyl or $CH_2OH$, X is O or S, NH or $NH(C_1-C_6$ alkyl), and m is 1, 2 or 3, may be prepared by reacting a compound of the formula

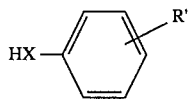

with a triflate compound of the formula

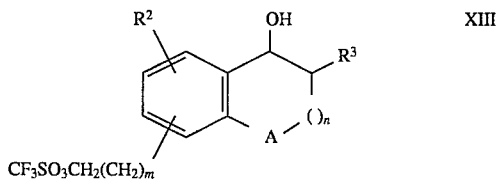

XIII in the presence of a base such as triethyl amine or sodium hydride in a reaction inert solvent.

The triflates may be prepared by reacting triflic anhydride with the compound of formula XXI wherein m is 0, 1 or 2, $R^4$ and $R^5$ are hydrogen, and $R^6$ is hydroxyl, the synthesis of which is described above.

The compounds of formula I wherein $R^1$ is —$CONR^7R^8$ may be prepared from the corresponding compound wherein $R^1$ is carboxy by reaction with an amine of the formula $NHR^7R^8$.

The salts of compounds of formula I containing a carboxy group may be prepared in a conventional manner by reaction with a base such as an alkali metal hydroxide, e.g., sodium hydroxide, or an alkaline earth metal hydroxide, e.g., magnesium hydroxide. The esters of compounds I containing a carboxy group may be prepared in a conventional manner by reacting the acid group with a $C_1-C_6$ alcohol, such as ethanol, phenyl ($C_1-C_6$) alcohol, $C_3-C_7$ cycloalkanol, phenol or phenol substituted by one to three of fluoro, chloro, $C_1-C_6$ alkyl or $C_1-C_6$ alkoxy.

The compounds of the invention can be administered to humans for the treatment of $LTB_4$ induced illnesses by various routes including orally, parenterally and topically, and through the use of suppositories and enemas. On oral administration dosage levels of about 0.5 to 1000 mg/day, advantageously about 5–500 mg/day, may be given in a single dose or up to 3 divided doses. For intravenous administration, dosage levels are about 0.1–500 mg/day, advantageously about 1.0–100 mg/day. Intravenous administration can include a continuous drip. Variations will necessarily occur depending on the age, weight and condition of the subject being treated and the particular route of administration chosen as will be known to those skilled in the art.

The compounds of the invention may be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules either alone or in admixture with excipients, or in the form of elixirs or suspensions containing flavoring or coloring agents. They can be injected parenterally, for example, intramuscularly, intravenously or subcutaneously. For parenteral administration, they are best used in the form of a sterile aqueous solution which can contain other solutes, for example, enough salt or glucose to make the solution isotonic.

The $LTB_4$ activity of the compounds of the invention may be determined by comparing the ability of the compounds of the invention to compete with radiolabelled $LTB_4$ for specific $LTB_4$ receptor sites on guinea pig spleen membranes. Guinea pig spleen membranes were prepared as described by Cheng et al. (J. Pharmacology and Experimental Therapeutics 232:80, 1985). The $^3H$-$LTB_4$ binding assay was performed in 150 µl containing 50 mM Tris pH 7.3, 10 mM $MgCl_2$, 9% Methanol, 0.7 nM $^3H$-$LTB_4$ (NEN, approximately 200 Ci/mmol) and 0.33 mg/ml guinea pig spleen membranes. Unlabeled $LTB_4$ was added at a concentration 5 µM to determine non-specific binding. Experimental compounds were added at varying concentrations to evaluate their effects on $^3H$-$LTB_4$ binding. The reactions were incubated at 4° C., for 30 minutes. Membrane bound $^3H$-$LTB_4$ was collected by filtration through glass fiber filters and the amount bound was determined by scintillation counting. The IC50 value for an experimental compound is the concentration at which 50% of specific $^3H$-$LTB_4$ binding is inhibited.

The following Examples illustrate the preparation of the compounds of the invention.

Example 1

A. 2',4'-Dihydroxy-3-chloropropiophenone

To a stirred mixture of resorcinol (200 g, 1.82 mol) and 3-chloropropionic acid (200 g, 1.84 mol) was added trifluoromethane sulfonic acid (1 kg) in one portion. The solution was heated slowly over 45 minutes to 80° C. then cooled to room temperature over 15 minutes and poured into chloroform (4.0 L). The organic portion was slowly poured into water (4.0 L) and the layers separated. The aqueous layer was extracted with chloroform (2×2.0 L). The combined organic layers were washed with brine, dried over sodium sulfate and filtered. Concentration in vacuo gave an orange semi-solid (244.1 g) which was used crude in the next step.

$^1H$-NMR (300 MHz, $CDCl_3$): 12.56 (1H, s), 7.63 (1H, d, J=7.6 Hz), 6.37–6.46 (2H, m), 3.92 (2H, t, J=6.3 Hz), 3.41 (2H, t, J=6.3 Hz).

B. 7-Hydroxybenzopyran-4-one

To a cooled (5° C.) solution of 2N sodium hydroxide (10.0 L) was added the compound of step A (244.1 g) in one portion. The solution was warmed to room temperature over 2 hours using a warm water bath then recooled to 5° C. and the pH adjusted to 2 with 6M sulfuric acid (1.2 L). The mixture was extracted with 3×3.0 L of ethyl acetate, washed with brine (1×2.0 L) dried over sodium sulfate and filtered. Concentration in vacuo gave a tan solid. Trituration with hexanes, and filtration afforded 173.7 g (58% yield) of the title compound.

M.P. 136° C.–137° C.

C. 7-[Trifluoromethylsulfonyloxy]-benzopyran-4-one

To a stirred solution of the compound of step B (173.7 g, 1.05 mole) in methylene chloride (3.0 L) at −78° C. was added triethylamine (320 g, 3.16 mole) and dimethylaminopyridine (2.5 g). After total dissolution, trifluoromethane sulfonic anhydride (327 g, 1.16 mole) was added dropwise over 20 minutes, the material was stirred for 30 minutes at −78° C., and then warmed to room temperature over 2 hours. The reaction mixture was poured into saturated ammonium chloride solution (2.5 L) and the layers separated. The aqueous layer was extracted with 2×2.0 L of methylene chloride. The combined organic fractions were washed with water (1×1.0 L), dried over magnesium sulfate and filtered. Concentration in vacuo gave a red oil. Chromatography over silica gel (1 kg) eluting with (8:1) hexane: ethyl acetate gave after solvent removal 211.1 g. (69% yield) of the title product.

M.P. 43°–44° C.

D. 7-[(Trifluoromethylsulfonyl)oxy]-3-phenymethylene-benzopyran-4-one

To a stirred solution of the product of Step C (27 g, 91.2 mmole) in 183 mL of methanol was added benzaldehyde (11.1 mL, 109 mmole) followed by pyrrolidine (9.1 mL, 109 mmole). The mixture was stirred at room temperature overnight, cooled to 0° C. and filtered. The solid was washed once with 50 mL of ice-cold methanol and then dried in vacuo; 35.2 g, (75% yield) of the title product was recovered.

M.P. 133°–135° C. $^1$H NMR (300 MHz, CDCl$_3$): 8.11 (1H, d, J=8.7 Hz), 7.91 (1H, bs), 7.40–7.51 (2H, m), 7.24–7.38 (3H, m), 6.97 (1H, dd, J=8.7 Hz, 2.4 Hz), 6.91 (1H, d, J=2.4 Hz), 5.40 (1H, bs).

E. 7-[(Trifluoromethylsulfonyl)oxy]-3-phenylmethyl-benzopyran-4-one

To a solution of the compound of step D (26.6 g, 69.2 mmole) in 250 mL of ethyl acetate in a 500 mL Parr shaker flask was added 10% palladium on carbon catalyst (1.3 g). The mixture was hydrogenated at 40 psi until hydrogen uptake ceased after about 3 hours. The mixture was filtered through celite (a tradename for diatamaceous earth) to remove the palladium catalyst, and chromatographed over silica gel (hexane-ether); 25.1 g (94% yield) of the title product was obtained M.P. 56°–58° C. $^1$H NMR (300 MHz, CDCl$_3$): 8.01 (1H, d, J=8.5 Hz), 7.20–7.35 (5H, m), 6.81–6.96 (2H, m), 4.42 (1H, dd, J=11.6, 4.4 Hz), 4.22 (1H, dd, J=11.6 Hz, 8.7 Hz), 3.26 (1H, dd, J=14.0, 4.4 Hz), 2.90–3.05 (1H, m), 2.70 (1H, dd, J=14.0, 8.7 Hz).

Example 2

A. 2-(3,Hydroxyphenyl) propanoic acid ethyl ester

A mixture of 100 g (0.658 mol) of 3-hydroxyphenylacetic acid, 6.0 ml concentrated sulfuric acid and 800 ml of ethanol was refluxed through a soxhlet with 3A molecular sieves for 3 hours. The reaction was cooled and concentrated to an oil on a rotovapor. The residue was added to 500 ml ice cold saturated sodium bicarbonate and 1 liter of ether. The ether extract was dried over magnesium sulfate and evaporated to give 116 g (98%) of ethyl 3-hydroxyphenylacetate as an oil.

To a 0° C. solution of 116 g (0.644 mol) of the above 3hydroxyphenylacetate in 645 ml dichloromethane and 64.6 ml (0.71 mol) dihydropyran was added a few crystals of 4-toluenesulfonic acid monohydrate. The reaction was stirred for 3 hours at 0° and then added to 200 ml saturated sodium bicarbonate. The organic extract was dried over magnesium sulfate and evaporated to give 161 g (95%) of 3-(tetrahydro-2H-pyran-2-yl)oxy]-phenylacetic acid ethyl ester as an oil.

To a 0° C. solution of 94.0 ml (0.671 mol) of diisopropylamine in 600 ml tetrahydrofuran was added 268 ml (0.671 mol) of 2.5M n-butyllithium in hexane. The resulting solution was cooled to −78° C. followed by a 30 minutes addition of 161 g (0.610 mol) of the above 3-[(tetrahydro-2H-pyran-2-yl)oxy]-phenylacetic acid ethyl ester in 160 ml tetrahydrofuran. The reaction mixture was stirred 10 minutes longer and then 45.6 ml (0.732 mol) of methyliodide was added in one portion. The reaction was allowed to warm to −15° C. over the next 20 minutes. The reaction mixture was quenched and hydrolyzed by addition of 580 ml of 6N sulfuric acid and heating to 48° C. for 15 minutes. The reaction was cooled and extracted with 1 liter ether. The ether extract was washed with 250 ml saturated sodium bicarbonate and 250 ml saturated sodium chloride. The extract was dried over magnesium sulfate, evaporated and the residue distilled to give 110 g (93%) of the title product.

B.P. (0.70 torr) 145°–147 ° C. $^1$H NMR (60 MHz, CDCl$_3$): 1.19 (t, J=7 Hz, CH3), 1.46 (d, J=7 Hz, CH$_3$), 3.65 (q, J=7 Hz, CH), 4.14 (q, J=7 Hz, CH$_2$), 6.02 (s, OH) and 6.7–7.4 (m, ArH).

B. 2-(3-(2-Cyanoethoxy]phenyl]propanoic acid ethyl ester

A mixture of 24.5 g (0.126 mol) of the compound of Example 2A, 61 ml t-butanol, 24.9 ml (0.378 mol) of acrylonitrile and 490 mg (8.75 mmol) of powdered potassium hydroxide was heated at 70° C. for 4 hours. An additional 15 ml (0.228 mol) of acrylonitrile and 100 mg (1.79 mmol) of powdered potassium hydroxide was added and the reaction heated one hour longer at 70° C. The reaction was cooled and concentrated on a rotovapor. The residue was dissolved in 200 ml ether and washed with three 200 ml portions of 0.5N sodium hydroxide. The organic extract was dried over magnesium sulfate and evaporated to give 9.44 g (30%) of the title product as an oil. Acidification of the combined basic extract with 4N hydrochloric acid, extraction with ether, drying of the ether extract over magnesium sulfate and evaporation gave 16.9 g of the crude starting compound 2-(3-hydroxyphenyl) acetic acid monohydrate.

Title Product:

$^1$H NMR (60 MHz, CDCl$_3$): 1.19(t, J=7 Hz, CH$_3$), 1.46 (d, J=7 Hz, CH$_3$), 2.76 (t, J=7 Hz, CH$_2$CN), 3.68 (q, J=7 Hz, CH), 3.95–4.2 (m, 2CH$_2$O) and 6.7–7.4 (m, ArH).

C. 2-(3-(2-Carboxyethoxy)phenyl)propanoic acid

A mixture of 9.44 g (38.2 mmol) of the compound of Example 2B and 23 ml of concentrated hydrochloric acid was heated at reflux for 6.5 hours. The reaction was cooled on ice, giving a solid that was filtered and washed with water. Vacuum drying gave 7.75 of crude product. The crude product was recrystallized from benzene to give 3.90 g (43%) of the title product.

M.P. 144°–146° (benzene). $^1$H NMR (300 MHz, d$_6$-DMSO): 1.35 (d, J=6 Hz, CH$_3$), 2.69 (t, J=6 Hz, CH2COO), 3.64 (q, J=6Hz, CH), 4.14 (t, J=6Hz, CH$_2$COO), 6.8 .(m, 3ArH) and 7.22 (dd, J=8 & 8 Hz, 1 ArH).

D. 3,4-Dihydro-α-methyl-4-oxo-2H-1-benzopyran-7-acetic acid methyl ester

A mixture of 35.8 g (0.150 mol) of 2-(3-(2-carboxyethoxy) phenyl) propanoic acid and 440 g of polyphosphoric acid was heated at 70° for 45 minutes. The hot reaction mixture was poured into 1.5 l ice-water. The quenched reaction was extracted three times with 300 ml of ethylacetate. The combined organic extract was washed once with 300 ml water, once with 300 ml saturated sodium chloride and then dried over magnesium sulfate. Evaporation gave 29.9 g (90%) of a solid as a mixture of acids. A solution of this crude mixture of acids (29.9 g, 0.136 mol) in 200 ml of acetone and a solution of 12.9 ml (0.136 mol) of dimethyl sulfate in 200 ml of acetone were simultaneously added over a period of one hour to a refluxing slurry of 22.4 g (0.162 mol) of potassium carbonate in 180 ml acetone. The resultant mixture was refluxed for one hour followed by addition of 1.3 ml (13.7 mmol) of dimethyl sulfate. The reaction was stirred for one hour further and then cooled and filtered. The filtrate was evaporated on a rotor evaporator to an oil. This oil was purified via column chromatography on 1.1 kg of silica gel eluted with 100% dichloromethane to 10% ether-dichloromethane to give in order of elution 15.3 g (48%) of the title product as a solid and 3.00 g (9%) of isomeric product, 3,4-dihydro-α-methyl-4-oxo-2H-1-benzopyran-5-acetic acid methyl ester.
Title Product:
$^1$H NMR (300 MHz, CDCl$_3$): 1.46 (d, J=7 Hz, CH3), 2.76 (t, J=6 Hz, CH$_2$), 3.65 (s, OCH$_3$), 4.50 (t, J=6 Hz, OCH$_2$), 6.88 (d, J=2 Hz, ArH), 6.92 (dd, J=8 & 2 Hz, C-6 ArH) and 7.82 (d, J=8 Hz, C-5 ArH).

E. 3,4-Dihydro-α-methyl-4-oxo-3-(phenylmethylene)-2-H-1-benzopyran-7-acetic acid methyl ester To a solution of 15.0 g (64.1 mmol) of the title compound of Example 2D and 64 ml (0.630 mol) of benzaldehyde was added 5.56 ml (64.1 mmol) of pyrrolidine. The reaction was stirred for 4 days and then purified via column chromatography on 750 g of silica gel eluted with 10–50% ether-hexane to give 19.2 g (95%) of the title compound as an oil.

$^1$H NMR (300 MHz, CDCl$_3$): 1.51 (d, J=6 Hz, CH$_3$), 3.69 (s, OCH$_3$), 3.74 (m, CH), 5.35 (d, J=2 Hz, CH$_2$O), 6.90 (d, J=2 Hz, C-8 ArH), 6.99 (dd, J=8 & 2 Hz, C-6 ArH), 7.25–7.55 (m, 5ArH), 7.86 (bs, vinyl H) and 7.97 (d, J=8 Hz, ArH).

F. 3,4-Dihydro-α-methyl-4-oxo-3-phenylmethyl-2H-1-benzopyran-7-acetic acid methyl ester A mixture of 19.1 g (59.3 mmol) of the compound of Example 2F and 250 mg of 5% palladium on carbon (50% water) in 150 ml methanol and 50 ml tetrahydrofuran (THF) was hydrogenated at 45 psi hydrogen in a Parr Apparatus for 1.75 hour. The reaction was filtered through supercel and evaporated to an oil (19.2 g, 100%). This material is used directly or purification can be achieved via column chromatography on 900 g of silica gel eluted with 50% etherhexane.

$^1$H NMR (300 MHz, CDCl$_3$), as a mixture of diastereomers, 1.50 (d, J=7 Hz, CH$_3$), 1.51 (d, J=7 Hz, CH3), 2.6–2.76 (m, PhCH), 2.82–2.96 (m, CH), 3.18–3.31 (m, PhCH), 3.68(s, OCH$_3$), 3.61 (q, J=7 Hz, CH), 4.08–4.2 (m, OCH), 4.27–4.4 (m, OCH), 6.86–6.97 (m, ArH), 7.15–7.41 (m, ArH) and 7.85 (d, J=8 Hz, ArH).

G. 3,4-cis and trans-3,4-Dihydro-4-hydroxy-α-methyl-3-phenylmethyl-2H-1-benzopyran-7-acetic acid methyl ester To a 0° C. solution of 19.2 g (59.3 mmol) of the compound of Example 2F, as a mixture of diastereomers, in 200 ml methanol and 100 ml tetrahydrofuran was added 3.38 g (88.9 mmol) of sodium borohydride. The reaction mixture was stirred 30 minutes and 0° C. and then added to 500 ml saturated sodium chloride. The quenched reaction mixture was extracted with three 500 ml portions of ether; the ether extracts were combined, dried over magnesium sulfate and evaporated to an oil. This crude oil was purified via column chromatography on 1 kg of silica gel eluted with 50% ether-hexane to yield in order of elution: 10.98 g (57%) of the cis isomer and 4.9 g (24%) of the trans isomer, both as mixtures of diastereomers.
Cis-isomer:
$^1$H NMR (300 MHz, CDCl$_3$): 1.48 (d, J=7 Hz, CH$_3$), 2.33 (m, CH), 2.69 (m, PhCH) 2.89 (m, PhCH) 3.65 (s, OCH$_3$) 3.66 (obscured by 3.65 s, CH) 4.09 (m, OCH$_2$), 4.50 (d, J=3.44 Hz, OCH), 6.78 (bs, ArH), 6.82 (bd, J=8 Hz, ArH), 7.16 (d, J=8 Hz, ArH) and 7.2–7.4 (m, 5ArH),
Trans - Isomer:
$^H$ $^{NMR}$ (300 MHz, CDCl$_3$): 1.50 (d, J=7 Hz, CH$_3$), 2.21 (m, CH), 2.53 (dd, J=13 & 8 Hz, PhCH), 2.71 (dd, J=13 & 6 Hz, PhCH), 3.67 (s, OCH3), 3.67 (obscured by 3.67 s, CH), 3.95 (dd, J=10& 6 Hz, OCH), 4.19 (dd, J=10 & 2 Hz, OCH), 4.47 (d, J=4.28 Hz, OCH), 6.79 (s, ArH), 6.86 (d, J=8 Hz, ArH), 7.15 (d, J=8 Hz, ArH) and 7.2–7.4 (m, 5ArH).

H. O-acetylmandelate ester diastereomers A and B of trans-3,4-dihydro-4,hydroxy-α-methyl-3-phenylmethyl-2H-1-benzopyran-7-acetic acid methyl ester A mixture of 2.58 g (7.91 mmol) of the trans-isomer of the compound of Example 2G (as a mixture of diastereomers), 1.84 g (9.49 mmol) of R-(−)-O-acetyl mandelic acid, 1.16 g (9.49 mmol) of 4-N,N-dimethylaminopyridine and 1.79 g (8.70 mmol) of dicyclohexyl-carbodiimide in 16 ml of dichloromethane was stirred at 25° C. for 16 hours. The reaction mixture was filtered and the filtrate evaporated to an oil. This crude oil was purified via column chromatography on 800 g silica gel eluted with 1–1.5% etherdichloromethane. Combination of pure fractions and rechromatography of less pure fractions yielded a total of 1.52 g (39%) of the less polar diastereomer A and 1.52 g (39%) of the more polar diastereomer B, each as a mixture of diastereomers and both of >95% purity.
Diastereomer A:
$^1$H NMR (300 MHz, CDCl$_3$): 1.44 (d, J=7 Hz, CH$_3$), 2.15 (s, CH$_3$), 2.33 (m, CH), 2.47 (dd, J=10 and 10 Hz, PhCH), 2.69 (dd, J=10 and 5 Hz, PhCH), 3.65 (s, OCH$_3$), 3.65 (obscured by 3.65 s, CH), 3.93 (m, OCH), 4.08 (m, OCH), 5.61 (d, J=2.57 Hz, OCH), 5.79 (s, CH), 6.69 (d, J=8 Hz, ArH), 6.76 (s, ArH), 6.80 (d, J=8 Hz, ArH) and 7.1–7.4 (m, 5ArH).
Diastereomer B:
$^1$H NMR (300 MHz, CDCl$_3$): 1.46 (d,J=7 Hz, CH$_3$), 1.99 (m, CH), 2.19 (s, CH$_3$), 2.36 (dd, J=12 and 9 Hz, PhCH), 2.51 (dd, J=12 and 6 Hz, PhCH), 3.68(s, OCH$_3$), 3.68 (obscured by 3.68s, CH), 3.79 (m, OCH$_2$), 5.69 (d,J=3.63, OCH), 5.86 (s, CH), 6.79 (d, J=2 Hz, ArH), 6.86 (dd,J=8 and 2 Hz, ArH), 7.02 (d,J=8 Hz, ArH) and 7.1–7.5 (m, 5 ArH).

I. Trans-3,4-Dihydro-4-hydroxy-α-methyl-3-phenylmethyl-2H-1-benzopyran-7-acetic acid, diastereomer A.

A mixture of 1.43 g (2.86 mmol) of diastereomer A from Example 2H, 16 ml of 1N sodium hydroxide and 16 ml methanol was heated at reflux for 90 minutes. The reaction mixture was cooled to 0° C. and acidified with 20 ml of 1N hydrochloric acid. The resultant mixture was saturated with sodium chloride, and then extracted with ethyl acetate. The ethyl acetate extract was evaporated to an oil. The crude oil was purified via column chromatography on 300 g of silica gel eluted with 25% ethyl acetate-dichloromethane to yield 810 mg (91%) of the title compound.

$[\alpha]^{22°}_D$=+25.05° (c=20.6 mg/ml, $CH_3OH$). IR($CHCl_3$): 3200 (b), 1706, 1620, 1604, 1575, and 1503 $Cm^1$. Anal. Calcd. for $C_{19}H_{20}O_4$: C 73.06, H 6.45 Found : C 72.66, H 6.79

J. Trans-3,4-Dihydro-4-hydroxy-α-methyl-3-phenylmethyl-2H-1-benzopyran-7-acetic acid, diastereomer B Using the method of Example 2 I, 1.43 g (2.86 mmole) of diastereomer B from Example 2H, 16 ml of 1N sodium hydroxide and 16 ml of methanol gave 344 mg (39%) of the title compound.

$[\alpha]_2^{22°}$=−32.67° (c=20.6 mg/ml, $CH_3OH$). ($CHCl_3$): 3200 (b), 1705, 1619, 1604, 1575 and 1502 $Cm^1$. Anal. Calcd for $C_{19}H_{20}O_4 \cdot \frac{1}{2}H_2O$: C, 72.23; H, 6.51 Found: C, 72.48; H, 6.42

K. Trans-3,4-Dihydro-4-hydroxy-α-methyl-3-phenylmethyl-2H-1-benzopyran-7-acetic acid sodium salt, diastereomer A To a solution of 705 mg (2.26 mmol) of diastereomer A of Example 2I in 50 ml of ethanol was added 2.26 ml (2.26 mmol) of 1N sodium hydroxide. The reaction was evaporated on a rotary evaporator and two additional 25 ml volumes of ethanol were added, followed by evaporation after each addition on the rotary evaporator. The solid obtained was then triturated first with dichloromethane and then hexane, followed by vacuum drying to give 642 mg (85%) of the title compound as a solid.

Anal. Calcd. for $C_{19}H_{19}O_4Na \cdot \frac{1}{2}H_2O$: C, 66.46; H, 5.87 Found: C, 66.22; H, 5.92

L. Trans-3,4-Dihydro-4-hydroxy-α-methyl-3-phenylmethyl-2-H-1-benzopyran-7-acetic acid sodium salt, diastereomer B Using the method of Example 2K, 292 mg (0.936 mmol) of diastereomer B of Example 2J and 0.94 ml of 1N sodium hydroxide gave 267 mg (85%) of the title compound as a solid.

Anal. Calcd. for $C_{19}H_{19}O_4Na \cdot \frac{1}{2}H_2O$: C, 66.46; H, 5.87 Found: C, 66.31; H, 5.92

Example 3

A. N-alpha-t-Butoxycarbonyl-D-tryptophan esters of the trans isomer of the compound of Example 2G.

To a solution of 8.02 g (24.6 mmol) of the trans isomer of Example 2G and 8.97 g (29.5 mmol) of N-α-t-butoxycarbonyl-D-tryptophan in 25 ml dichloromethane was added 5.57 g (27.0 mmol) of dicyclohexylcarbodiimide. The reaction mixture was then stirred for 3 hours at 25° C. and filtered, and the filtrate was evaporated to an oil. This crude oil was purified via column chromatography on 2 kg of silica gel eluted with 3–10% ether-dichloromethane to yield a less polar diastereomer A (7.24 g, 48%) and a more polar diastereomer B (6.97 g, 46%), each as a mixture of diastereomers, of the title compound.

Diastereomer A Ester
$^1$H NMR (300 MHz, $CDCl_3$): 1.42 (s, C($CH_3$)3), 1.56 (d, J=6 Hz, $CH_3$), 2.10 (m, CH), 2.5 (m, 2H), 3.1 (m, 1H), 3.23 (m, 1H), 3.75 and 3.79 (s, $OCH_3$), 3.7 (m, 2H obscured by 3.75 and 3.79 s), 4.66 (m, 1H), 5.07 (m, 1H), 5.55 and 5.99 (s, NH), 5.93 and 6.03 (s, NH), 6.8 (m, 2ArH), 6.9–7.16 (m, 4ArH), 7.25 (m, 5ArH), 7.52 (bd, 1ArH) and 8.26 and 8.35 (s, 1H). $[\alpha]^{25°}_D$=+68.92° (c=24.3 mg/ml, $CH_3OH$).

Diastereomer B Ester
$^1$H NMR (300 MHz, $CDCl_3$): 1.38 (s, C($CH_3$)$_3$), 1.48 (d, J=7 Hz, $CH_3$), 1.83 (m, CH), 2.35–2.6 (m, 2H), 3.1–3.4 (m, 2H), 3.69 (s, $OCH_3$), 3.7 (m, obscured by 3.69s, 2H), 4.61 (m, 1H), 5.1 (m, 1H), 5.59 (bs, NH), 6.7–6.85 (m, 3ArH), 7–7.4 (m, 8 ArH), 7.55 (m, 1ArH) and 8.10 (bs, 1H). $[\alpha]^{25°}_D$=−91.05° (c=20.8 mg/ml, $CH_3OH$).

B. Trans-3,4-Dihydro-4-hydroxy-α-methyl-3-phenylmethyl-2H-1-benzopyran-9-acetic acid-diastereomer B Using the method of Example 2I, 6.87 g (11.2 mmol) of diastereomer B of Example 3A gave 2.52 g (69%) of diastereomer B of the title compound as a mixture of diastereomers.

$[\alpha]^{20°}_D$=−34.53° (c=10.8 mg/ml, $CH_3OH$). $^1$H NMR (300 MHz, $D_6$-DMSO-NaOD-$D_2$O): 1.23 (d, J=7 Hz, $CH_3$), 2.05 (m, CH), 2.42 (dd, J=13.7 & 8.9 Hz, CH), 2.68 (dd, J=13.7 & 6.2 Hz, CH), 3.29 (9, J=7 Hz, CH), 3.83 (dd, J=10.8 & 5.1 CH), 4.07 (dd, J=10.8 & 2.5 Hz, CH), 4.23 (d, J=4.6 Hz, CH), 6.68 and 6.71 (d, J=2 Hz, ArH), 6.82 and 6.84 (dd, J=7 & 2 Hz, ArH) and 7.13–7.37 (m, 6ArH).

C. Trans-3,4-Dihydro-4-hydroxy-alpha-methyl-3-phenylmethyl-2H-1-benzopyran-7-acetic acid using the method of Example 2I, 7.14 g (11.7 mmol) of diastereomer A of Example 3B gave a crude product that was purified via column chromatography on 280 g of silica gel eluted with 3% acetic acid-chloroform to give 2.75 g (72%) of diastereomer A of the title compound as a mixture of diastereomers.

$[\alpha]^{20°}$=+33.00° (c=11.05 mg/ml, $CH_3OH$). $^1$H NMR (300 MHz, $D_6$-DMSO-NaOD-$D_2$O): 1.21 (d, J=7 Hz, $CH_3$), 2.06 (m, CH), 2.42 (dd, J=13.6 and 8.8 Hz, CH), 2.67 (dd, J=13.7 and 6.3 Hz, CH), 3.23 (q, J=7 Hz, CH), 3.83 (dd, J=11 and 5 Hz, CH), 4.06 (dd, J=10.8 and 2.5 Hz), 4.24 (d, J=4.5 Hz, CH), 6.69 and 6.72 (d, J=2 Hz, ArH), 6.82 and 6.84 (dd, J=8 and 2 Hz, ArH) and 7.11–7.33 (m, 6ArH).

D. Trans-3,4-Dihydro-4-hydroxy-α-methyl-3-phenylmethyl-2H-1-benzopyran-7-acetic acid-enantiomers A1 and A2.

Diastereomer A of Example 3C (812 mg) was fractionally crystallized from acetone-hexane to yield 111 mg (14%) of a higher melting diastereomer, enantiomer A1, and 100 mg (12%) of a lower melting diastereomer, enantiomer A2.

Enantiomer A1
M.P.=182°–183.5° C. $^1$H NMR (300 MHz, $D_6$-DMSO): 1.32 (d, J=7 Hz, $CH_3$), 2.1 (m, CH), 2.42 (dd, J=13.7 & 9.0 Hz, CH), 2.71 (dd, J=13.7 and 6.1 Hz, CH), 3.59 (q, J=7 Hz, CH), 3.86 (dd, J=10.9 & 5.5 Hz, CH), 4.08 (dd, J=10.9 & 2.7 Hz, CH), 4.27 (d, J=4.7 Hz, CH), 5.47 (bs, OH), 6.68 (d, J=2 Hz, ArH), 6.83 (dd, J=8 & 2 Hz, ArH) and 7.17–7.34 (m, 6ArH). $[\alpha]^{23°}_D$=+71.10 (c=20 mg/ml, $CH_3OH$). Anal. calcd. for $C_{19}C_{20}O_4$: C, 73.06; H, 6.45 Found: C, 72.75; H, 6.42

Enantiomer A2

M.P. 160.5°–161.5° C. $^1$H NMR (300 MHz, D$_6$-DMSO): 1.32 (d, J=7 Hz, CH$_3$), 2.1 (m, CH), 2.41 (dd, J=1.37 & 9 Hz, CH), 2.71 (dd, J=13.6 & 6.1 Hz, CH), 3.59 (d, J=7 Hz, CH), 3.86 (dd, J=11 & 5.4 Hz, CH), 4.08 (dd, J=11 & 2.7 Hz, CH), 4.27 (d, J=4.6 Hz, CH), 5.46 (bs, OH), 6.68 (d, J=2 Hz, ArH), 6.83 (dd, J=8 & 2 Hz, ArH) and 7.17–7.34 (m, 6 ArH). $[\alpha]^{23°}{}_D$=+5.15° (c=20 mg/ml, CH$_3$OH) Anal. calcd. for C$_{19}$H$_{20}$O$_4$: C, 73.06; H, 6.45 Found: C, 72.71; H, 6.33

E. Trans-3,4-Dihydro-4-hydroxy-α-methyl-3-phenylmethyl-2H-1-benzopyran-7-acetic acid Diastereomer B of Example 2J (1.02 g) was fractionally crystallized from acetone-hexane to yield 168 mg (16%) of a higher melting diastereomer, enantiomer B2.

Enantiomer B1

M.P.=182°–184 ° C. $^1$H NMR (300 MHz, D$_6$-DMSO): 1.32 (d, J=7 Hz, CH$_3$), 2.05 (m, CH), 2.42 (dd, J=13.7 & 9 Hz, CH), 2.71 (dd, J=13.7 & 6 Hz, CH), 3.59 (q, J=7 Hz, CH), 3.86 (dd, J=11 and 5.4 Hz, CH), 4.08 (dd, J=11 & 2.7 Hz, CH), 4.28 (bs, CH), 5.46 (bs, OH), 6.68 (d, J=2 Hz, ArH), 6.83 (dd, J=8 & 2 Hz, ArH) and 7.17–7.37 (m, 6 ArH). $[\alpha]^{23°}{}_D$=−70.84° (c=20 mg/ml, CH$_3$OH) Anal. calcd. for C$_{19}$H$_{20}$O$_4$: C, 73.06; H, 6.45 Found: C, 72.73; H, 6.43

Enantiomer B2

M.P.=161°–162.5° C. $^1$H NMR (300 MHz, D$_6$-DMSO): 1.32 (d, J=7 Hz, CH$_3$), 2.05 (m, CH), 2.41 (dd, J=13.7 & 9 Hz, CH), 2.71 (dd, J=13.7 & 6.1 Hz, CH), 3.59 (q, J=7 Hz, CH), 3.86 (dd, J=12 & 5.5 Hz, CH), 4.08 (dd, J=12 & 2.7 Hz, CH), 4.27 (d, J=4.7 Hz, CH), 5.46 (bs, OH), 6.68 (d, J=2 Hz, ArH), 6.83 (dd, J=8 & 2 Hz, ArH), 7.17–7.34 (m, 6 ArH). $[\alpha]^{23°}{}_D$=−4.92° (c=20 mg/ml, CH$_3$OH) Anal. calcd. for C$_{19}$H$_{20}$O$_4$: C, 73.06; H, 6.45 Found: C, 72.89; H, 6.42

Example 4

A. Ethyl 2-(3-phenylmethyl-4-chroman-7-yl)cyclopentanecarboxylic acid

3-Benzyl-7-trifluoromethylsulfonyloxy-4-chromanone (35.0 g, 91.0 mmole) was dissolved in a mixture of dimethylformamide (230 mL) and dimethoxyethane (230 mL). To this solution was added in the following order, tris(2-methylphenyl)phosphine (7.48 g, 24.6 mmole), bis(benzonitrile)palladium(II) chloride (2.44 g, 6.37 mmole), the trimethylsilyl ketene acetal of ethyl cyclopentanecarboxylate (29.26 g, 136.5 mmole), and a 1.0M ethereal solution of zinc chloride (25 mL, 25 mmole). The resulting clear yellow solution was refluxed for 1 hour. Additional trimethylsilyl ketene acetal (9.75 g, 45.5mmole) was added at this point and the reflux continued for another 1 hour. The cooled mixture was diluted with water (1 L) and extracted with ether. The combined ether extracts were washed with water (1 L) and then dried over magnesium sulfate. Filtration and concentration of the extract gave a yellow oil which was chromatographed on silica gel (8:92—ethyl acetate/hexane). This yielded 22.13 (64%) of white solid;

m.p. 50°–56° C.; $^1$H NMR (CDCl$_3$): 1.23 (t, J=7.0 Hz, 3H), 1.75 (m, 4H), 1.9 (m, 2H), 2.6 (m, 2H), 2.70 (dd, J=10.5, 13.8 Hz, 1H), 2.9 (m, 1H), 3.26 (dd, J=4.3, 13.8 Hz, 1H), 4.08 (d, J=7.0 Hz, 2H), 4.15 (dd, J=8.2, 11.5 Hz, 1H), 4.35 (dd, J=4.3, 11.5 Hz), 6.95 (d, J=1.7 Hz, 1H), 7.02 (dd, J=1.7, 8.3 Hz, 1H), 7.2–7.4 (m, 5H), 7.84 (d, J=8.3 Hz, 1H).

B. Ethyl 2-(4-hydroxy-3-(phenylmethyl)chroman-7-yl)cyclopentanecarboxylate

The compound of step A (111.99 g, 295.9 mmole) was dissolved in ethanol (2.5 L) and cautiously treated with sodium borohydride (12.3 g, 325.5 mmole) at room temperature. After 3 hours the reaction mixture was concentrated to a small volume and diluted with ether. The ether was washed with saturated sodium bicarbonate solution and dried over sodium sulfate. The extract was filtered and concentrated to an oil which was chromatographed on silica gel (20:80—ethyl acetate/hexane). This gave 63.4 g (56%) of the higher R$_f$ product, ethyl 2-((3R*, 4R*)-4-hydroxy-3-(phenylmethyl)-chroman-7-yl)cyclopentanecarboxylate as an oil;

hu 1H NMR (CDCl$_3$): 1.15 (t, J=7.1 Hz, 3H), 1.7 (m, 4H), 1.8–1.9 (m, 2H), 2.3 (m, 1H), 2.5–2.6 (m, 2H), 2.66 (dd, J=7.2, 13.6 Hz, 1H), 2.86 (dd, J=8.4, 13.6 Hz, 1H), 4.0–4.1 (m, 4H), 4.47 (br t, 1H), 6.85 (d, J=1.8 Hz, 1H), 6.88 (dd, J=1.8, 7.9 Hz, 1H), 7.12 (d, J=7.9 Hz, 1H), 7.1–7.35 (m, 5H); and 43.3 g (38%) of the lower R$_f$ product, ethyl 2-((3S*, 4R*)-4-hydroxy-3-(phenylmethyl)-chroman-7-yl)cyclopentanecarboxylate as an oil:

hu 1H-NMR (CDCl$_3$):1.17 (t, J=7.0 Hz, 3H), 1.7 (m, 4H), 1.8–1.9 (m, 2H), 2.2 (m, 1H), 2.52 (dd, J=9.3, 13.7 Hz, 1H), 2.6 (m, 2H), 2.70 (dd, J=6.3, 13.7 Hz, 1H), 3.95 (dd, J=3.7, 11.2 Hz, 1H), 4.07 (q, J=7.0 Hz, 2H), 4.18 (dd, J=2.6, 11.2 Hz, 1H) 4.47 (br, t, 1H), 6.88 (d, J=1.8 Hz, 1H), 6.94 (dd, J=1.8, 8.0, 1H), 7.15–7.3 (m, 6H).

C. Ethyl 2-((3S*, 4R*)-4-(4-methoxyphenoxy)-3-(phenylmethyl)chroman-7-yl)cyclopentanecarboxylate To ethyl 2-((3R*, 4R*)-4-hydroxy-3-(phenylmethyl)-chroman-7-yl) cyclopentanecarboxylic acid (63.4 g, 167 mmole), triphenylphosphine (65.6 g, 250 mmole), and 4-methoxyphenol (62.1 g, 500 mmole) in tetrahydrofuran (1.9 L) was added diethyl azodicarboxylate (43.6 g, 250 mmole) in one portion at room temperature. After 15 minutes at room temperature, the reaction mixture was refluxed for 1 hour. The cooled mixture was then concentrated under reduced pressure and the residual oil dissolved in ether. The ether was washed with 0.1N sodium hydroxide solution, 1.0N hydrochloric acid and water. The extract was dried with magnesium sulfate, filtered and concentrated to an oily solid. This was chromatographed on silica gel (10:90—ethyl acetate/hexane) to give 47.7 g (58.8%) of pure product as an oil:

$^1$H NMR (CDCl$_3$): 1.19 (t, J=7.1 Hz, 3H), 1.7 (m, 4H), 1.8–1.9 (m, 1H), 2.4 (m, 1H), 2.6–2.7 (m, 4H), 3.76 (s, 3H), 4.02 (br d, J=11.0 Hz, 1H), 4.06 (d, J=7.1 Hz, 2H),4.28 (dd, J=2.3, 11.0, 1H), 4.85 (br s, 1H), 6.66 (d, J=9.1 Hz, 2H), 6.74 (d, J=9.1 Hz, 2H), 6.95 (m, 2H), 7.1-7.2 (m, 3H), 7.2–7.35 (m, 3H).

D. Ethyl 2-((3S*, 4R*)-4-hydroxy-3-(phenylmethyl-chroman-7-yl)cyclopentanecarboxylate The compound of step C (47.7 g, 98.1 mmole) was dissolved in a mixture of acetonitrile (3.0 L) and water (750 mL) and cooled to 5° C. Ceric ammonium nitrate (134 g, 245 mmole) was added in one portion and the mixture stirred for 20 minutes at 5° C. The mixture was then diluted with ethyl acetate and washed with saturated sodium chloride solution and saturated sodium bicarbonate solution. The extract was then dried with sodium sulfate, filtered and concentrated to an oil. This was chromatographed on silica gel (15:85—ethyl acetate/hexane) giving 24.78 g (66.4%) of pure product which was identical to the compound prepared by the sodium borohydride reduction of the compound of step A.

E. N-α-t-Butoxycarbonyl-D-tryptophan ((3S, 4R)-3-benzyl-7-(1-carboethoxycyclopentyl)chroman-4-yl) ester The compound of step D (68.17 g, 179 mmole), N-α-t-BOC (butoxycarbonyl)-D-tryptophan (65.52 g, 215 mmole), and 4-dimethylaminopyridine (24.1mmole, 197 mmole) were dissolved in dry methylene chloride (1.8 L) and treated in one portion with dicyclohexylcarbodiimide (40.7 g, 197 mmole) at room temperature. After 12 hours the reaction was filtered and the filter cake was held with methylene chloride. The filtrate was washed with 1N hydrochloric acid (2 times 400 mL) and saturated sodium bicarbonate solution (400 mL). The methylene chloride was then dried over magnesium sulfate, filtered and concentrated in vacuo. The residual oil was chromatographed on silica gel (20:80—ethyl acetate/hexane) to give 55.30 g (46.3%) of the title product, $^1$H-NMR (CDCl$_3$): 1.25 (t, 3H), 1.43 (s, 9H), 1.75 (m, 4H) 2.0 (m, 2H) 2.1 (m, 1H), 2.4–2.7 (m, 4H),3.09 (dd, 1H), 3.22 (dd, 1H), 3.7 (m, 2H), 4.2 (m, 2H), 4.65 (m, 1H), 5.1 (d, 1H), 5.6 (s, 1H), 5.9 (s, 1H), 6.9 (m, 2H), 7.0 (m, 1H), 7.1 (m, 3H), 7.2–7.3 (m, 5H), 7.51 (d, 1H), 8.2 (s, 1H); and 48.56 g (40.7%) of the lower R$_f$ product, N-α-t-butoxycarbonyl-D-tryptophan ((3R, 4S)-3-benzyl-7-(1-carboethoxycyclopentyl)-chroman-4-yl) ester: m.p. 76°–80° C.;

$^1$H MNR (CDCL$_3$): 1.20 (t, 3H), 1.39 (s, 9H), 1.7 (m, 4H), 1.8–1.95 (m, 3H), 2.40 (dd, 1H), 2.51 (dd, 1H), 2.55–2.6 (m, 2H), 3.18 (dd, 1H), 3.29 (dd, 1H), 3.7 (m, 3H), 4.11 (q, 2H), 4.6 (m, 1H), 4.98 (d, 1H), 5.58 (s, 1H), 6.73 (d, 1H), 6.8–6.85 (m, 2H), 7.0–7.3 (m, 8H), 7.53 (d, 1H), 8.06 (s, 1H).

F. 2-((3S, 4R)-4-Hydroxy-3-(phenylmethyl)chroman-7-yl)cyclopentanecarboxylic acid The title compound of Step E (55.3 g, 82.9 mmole) was refluxed in a 1:1 mixture of 1.0N sodium hydroxide and ethanol (1660 mL) for 17 hours. The cooled mixture was acidified with 1.0M sulfuric acid (450 mL) and then diluted with water (500 mL). This mixture was extracted with ether (1500 mL, 500 mL). The combined ether extracts were washed with saturated sodium chloride solution and dried over magnesium sulfate. Filtration and concentration of the extract gave a glass which was chromatographed on silica gel (5:10:85—acetic acid/ethyl acetate/hexane). This gave 24.19 g (82.8%) of product which was recrystallized from cyclohexane/ethyl acetate yielding 21.28 g (72.9%) of white solid;

M.p. 164°–165° C.; $^1$H NMR (CDCl$_3$): 1.7 (m 4H), 1.9 (m, 2H), 2.2 (m, 2H), 2.5–2.75 (m, 3H), 3.95 (dd, J=3.8, 11.3 Hz, 1H), 4.19 (dd, J=2.6, 11.2 Hz, 1H), 4.47 (d, J=3.9 Hz, 1H), 6.09 (d, J=1.8 Hz, 1H), 6.97 (dd, J=1.8, 8.0 Hz, 1H), 7.15–7.3 (m, 6H); [α]$_D$°: =29.9°.

Example 5

A. Ethyl 2-((3S*, 4R*)-4-1,1-dimethylethyl)dimethysilyloxy -3-(phenylmethyl)-chroman-7-yl)cyclopentanecarboxylate Ethyl 2-((3S*, 4R*) -4-hydroxy-3-(phenylmethyl)-chroman -7-yl)cyclopentanecarboxylic acid (4.71 g, 12.9 mmole), (2,2-dimethylethyl) dimethylsilyl chloride (2.52 g, 16.7), and imidazole (1.10 g, 16.7 mmole) were combined in dry DMF (64 mL) and stirred at room temperature for 24 hours. The mixture was diluted with ether, washed with water three times, dried, filtered and concentrated to give an oil which was used as is.

$^1$H NMR (CDCl$_3$): 0.00 (s,6H), 0.82 (s, 9H), 1.18 (t, 3H), 1.7 (m, 4H), 1.9 (m, 2H), 2.05 (m, 1H), 2.50 (d, 2H), 2.6 (m, 2H), 3.99 (dd, 1H), 4.10 (q, 2H), 4.26 (dd, 1H), 4.39 (br s, 1H), 6.9 (m, 2H), 7.05–7.3 (m, 6H).

B. 2-((3S*, 4R*)-4-(1,1-dimethylethyl)dimethylsilyloxy -3-(phenylmethyl)chroman-7-yl)cyclopentanecarbonitrile A mixture of trimethylaluminum (18.6 mL, 2.0M in toluene, 37.3 mmole) in xylene (70 mL) was saturated with ammonium gas. The ester of step A (4.10 g, 9.32 mmole) was added and the mixture refluxed until the ester was consumed. The cooled mixture was quenched with water and filtered to remove precipitated aluminum salts. The filtrate was diluted with ethyl acetate, washed with 1N HCl and saturated sodium bicarbonate solution, dried, filtered and concentrated to an oil. The oil was chromatographed to give 1.83 g of the desired nitrile.

$^1$H NMR (CDCl$_3$): 0.00 (s, 6H), 0.83 (s, 9H), 1.9–2.2 (m, 9H), 2.4–2.55 (m, 4H), 4.00 (dd, 1H), 4.28(dd, 1H), 4.49 (br s, 1H), 6.93 (d, 1H), 7.02 (dd, 1H), 7.1 (m, 3H), 7.2–7.3 (m, 3H).

C. 5-(1-((3S*, 4R*)-4-(1,1-dimethylethyl)dimethylsilyloxy -3-(phenylmethyl]chroman-7-yl)cyclopent-1-yl)-1-trimethylstannyltetrazole The nitrile of Step B (700 mg, 1.56 mmole) and trimethylstannyl azide (1.22 g, 5.92 mmole) were refluxed together in dry toluene (20 mL) for 72 hours. The cooled reaction mixture was filtered and the filtrate concentrated to an oil which was chromatographed to give 620 mg of the tetrazole as an oil.

$^1$H NMR (CDCl$_3$): 0.00 (S, 6H), 0.85 (S, 9H), 1.9 (m, 3H), 2.05 (m, 2H), 2.09 (s, 9H), 2.3–2.4 (m, 2H), 2.52 (d, 2H), 2.6 (m, 2H), 4.01 (dd, 1H), 4.28 (dd, 1H), 4.40 (br s, 1H), 6.8–6.9 (m, 2H), 7.1–7.15 (m, 3H), 7.2–7.35 (m, 3H).

D. 5-(1-((3S*, 4R*)-4-hydroxy-3-(phenylmethyl)chroman-7-yl)-cyclopent-1-yl)-tetrazole The stannyltetrazole of Step C (620 mg, 0.94 mmole) and tetrabutylammonium fluoride (2.8 mL, 1.0M in THF, 2.8 mmole) in dry THF (10 mL) were stirred at room temperature for 72 hours. The mixture was diluted with ethyl acetate, washed with 1N HCl, dried, filtered and concentrated. The resulting oil was chromatographed to give 13 mg of destannylated product, 43 mg of the desired destannylated and desilylated material, and 286 mg of desilylated product. The desilylated product was dissolved in THF (10 mL) and treated with tetrabutylammonium fluoride (2.8 mL, 1.0M in THF, 2.8 mmole). After 5 days at room temperature the mixture was worked-up as before and chromatography gave 87 mg of the title compound as a white foam.

$^1$H-NMR (CDCl$_3$): 1.9–2.1 (m, 6H), 2.2 (m, 1H), 2.45 (m, 2H), 2.51 (dd, J=9.2, 13.8 Hz, 1H), 2.71 (dd, J=6.5, 13.8 Hz, 1H), 3.98 (dd, J=4.4, 11.1 Hz, 1H), 4.21 (dd, J=2.6, 11.1 Hz, 1H), 4.49 (d, J=4.0 Hz, 1H), 6.94 (d, J=2.0 Hz, 1H), 7.08 (dd, J=2.0, 8.0 Hz, 1H), 7.15–7.35 (m, 6H).

Example 6

((3S*, 4S*)-4-Hydroxy-3-(phenylmethyl)-chroman-7-yl)-dimethylacetic acid sodium carboxylate salt Using the method of Example 4F, methyl ((3S*, 4S*)-4-hydroxy-3-(phenylmethyl)-chroman-7-yl)dimethylacetate (226 mg, 0.66 mmole) gave 212 mg (98%) of the acid as a foam. Treatment of this with an equivalent of sodium hydroxide in ethanol followed by concentration yielded 245 mg of the sodium salt as a pale orange foam:

$^1$H NMR (d$_6$-Me$_2$SO): 1.29 (s, 6H), 2.25 (m, 1H), 2.55 (m, 1H) (largely obscured by the d$_5$-Me$_2$SO peak), 2.79 (dd, J=7.5, 13.4 Hz, 1H), 3.95 (m, 2H), 4.31 (br s, 1H), 5.25 (br s, 1H), 6.74 (br s, 1H), 6.86 (br d, J=8.0 Hz, 1H), 7.02 (d, J=8.0 Hz, 1H), 7.1 (m, 1H), 7.2 (m, 3H).

Example 7

((3S*,4R*)-4-Hydroxy-3-(phenylmethyl)-chroman-7yl)-dimethylacetic acid sodium carboxylate salt Using the method of Example 4F, methyl ((3S*,4R*)-4-hydroxy-3- (phenylmethyl) chroman-7-yl) dimethylacetate (214 mg, 0.63 mmole) gave 180 mg (88%) of the acid as an oil. Treatment of this with an equivalent of sodium hydroxide in ethanol followed by concentration yielded 212 mg of the sodium salt as a light tan foam:

$^1$H NMR (d$_6$-Me$_2$SO): 1.32 (s, 6H), 2.05 (m, 1H), 2.43 (dd, J=9.0, 13.7 Hz, 1H), 2.67 (dd, J=6.1, 13.7 Hz, 1H), 3.82 (dd, J=5.1, 10.8 Hz, 1H), 4.06 (dd, J=2.5, 10.8 Hz, 1H), 4.23 (d, J=4.5 Hz), 6.76 (d, J=1.5 Hz, 1H), 6.92 (br d, J=8.0 Hz, 1H), 7.1–7.5 (m, 6H).

Example 8

2-((3S*,4R*)-4-Hydroxy-3-(phenylmethyl)chroman-7-yl)-cyclopentanecarboxylic acid Using the method of Example 4F, the title compound of Example 4B (the lower R$_f$ product, 1.00 g, 2.63 mmole) gave after recrystallization (cyclohexane-ethyl acetate (EtOAc)) 758 mg (82%) of a white crystalline solid:

mp 153°–155° C., $^1$H NMR (CDCl$_3$): 1.75 (m, 4H), 1.9 (m, 2H), 2.2 (m, 2H), 2.51 (dd, J=9.3, 13.7 Hz, 1H), 2.6 (m, 2H), 2.70 (dd, J=6.3, 13.7 Hz, 1H), 3.94 (dd, J=4.2, 11.1 Hz, 1H), 4.18 (dd, J=2.6, 11.1 Hz, 1H), 4.47 (d, J=4.0 Hz, 1H), 6.90 (d, J=1.8 Hz, 1H), 6.98 (dd, J=1.8, 8.0 Hz, 1H), 7.15–7.35 (m 6H); mass spectrum, m/e (relative intensity): M$^+$352 (56), 260 (100), 215 (27), 189 (17), 161 (26), 107 (21), 91 (73). Anal. calc'd for C$_{22}$H$_{24}$O$_4$: C, 74.80; H, 6.86. Found: C, 74.98; H. 6.90.

Example 9

2-((3R*,4R*)-4-Hydroxy-3-(phenylmethyl)chroman-7-yl)-cyclopentanecarboxylic acid Using the method of Example 4F, the title compound of Example 4B (the higher R$_f$ product, 2.35 g, 6.18 mmole) gave after recrystallization (cyclohexane-EtOAc) 800 mg (37%) of a white crystalline solid:

mp 129°–130° C., $^1$H NMR (CDCl$_3$): 1.70 (m, 4H), 1.8–1.9 (m, 2H), 2.3 (m, 2H), 2.5–2.6 (m, 2H), 2.66 (dd, J=7.2, 13.7 Hz, 1H), 2.85 (dd, J=8.5, 13.7 Hz, 1H), 4.06 (d, J=7.9 Hz, 2H), 4.46 (d, J=3.0 Hz, 1H), 6.86 (d, J=1.8 Hz, 1H), 6.90 (dd, J=1.8, 8.0 Hz, 1H), 7.13 (d, J=8.0 Hz, 1H), 7.2–7.4 (m, 5H).

Example 10

2-((3S*,4R*)-4-Hydroxy-3-(phenylmethyl)chroman-7-yl-cyclohexanecarboxylic acid

Using the method of Example 4F with methanol as the solvent, methyl 2-((3S*, 4R*)-4-hydroxy-3-(phenylmethyl) chroman-7-yl)cyclohexanecarboxylate (543 mg, 1.43 mmole) gave after recrystallization (cyclohexane-EtOAc) 389 mg (74%) of a white crystalline solid:

m.p. 169°–170° C., $^1$H NMR (CDCl$_3$): 1.25–1.35 (m, 2H), 1.5–1.6 (m, 2H), 1.6–1.8 (m, 4H), 2.2 (m, 1H), 2.4–2.5 (m, 2H), 2.51 (dd, J=9.4, 13.8 Hz, 1H), 2.70 (dd, J=6.3, 13.8 Hz, 1H ), 3.95 (dd, J=4.3, 11.2 Hz, 1H), 4.17 (dd, J=2.6, 11.2 Hz, 1H), 4.47 (d, J=3.9 Hz, 1H), 6.95 (d, J=1.9 Hz, 1H), 7.03 (dd, J=1.9, 8.1 Hz, 1H), 7.15–7.35 (m, 6H).

Example 11

2-((3S,4R)-4-Hydroxy-3-(phenylmethyl)chroman-7-yl)cyclohexanecarboxylic acid

Using the method of Example 4F, N-α-t-butoxycarbonyl-D-tryptophan ((3S, 4R)-3-benzyl-7-(1-carbomethoxycyclohexyl) chroman-4-yl) ester (7.95 g, 12.0 mmole) gave after chromatography (5:10:85—acetic acid (HOAc): EtOAc: hexane) and recrystallization (cyclohexane-EtOAc) 1.60 g (36%) of a white crystalline solid:

m.p. 166°–167° C., [α]$_D$+6.8°; $^1$H NMR (CDCl$_3$): 1.25–1.35 (m, 2H), 1.5–1.6 (m, 2H), 1.6–1.8 (m, 4H), 2.2 (m, 1H), 2.4–2.5 (m, 2H), 2.51 (dd, J=9.4, 13.8 Hz, 1H), 2.70 (dd, J=6.3), 13.8 Hz, 1H), 3.95 (dd, J=4.3, 11.2 Hz, 1H), 4.17 (dd, J=2.6, 11.2 Hz, 1H), 4.47 (d, J=3.9 Hz, 1H), 6.95 (d, J=1.9 Hz, 1H), 7.03 (dd, J=1.9, 8.1 Hz, 1H), 7.15–7.35 (m, 6H).

Example 12

2-((3R,4S)-4-Hydroxy-3-(phenylmethyl)chroman-7-yl)-cyclohexanecarboxylic acid

Using the method of Example 4F, N-α-t-butoxycarbonyl-D-tryptophan ((3R, 4S)-3-benzyl-7-(1-carbomethoxycyclohexyl) chroman-4-yl) ester (7.40 g, 11.1 mmole) gave after chromatography 5:10:85—HOAc:EtOAc:hexane) and recrystallization (cyclohexane-EtOAc) 1.19 g (29% ) of a white crystalline solid:

mp 165°–167° C., [α]$_D$–10.2°; $^1$H-NMR (CDCl$_3$): 1.25–1.35 (m, 2H), 1.5–1.6 (m, 2H), 1.6–1.8 (m, 4H), 2.2 (m, 1H), 2.4–2.5 (m, 2H), 2.51 (dd, J=9.4, 13.8 Hz, 1H), 2.70 (dd, J=6.3, 13.8 Hz, 1H), 3.95 (dd, J=4.3, 11.2 Hz, 1H), 4.17 (dd, J=2.6, 11.2 Hz, 1H), 4.47 (d, J=3.9 Hz, 1H), 6.95 (d, J=1.9 Hz, 1 H), 7.03 (dd, J=1.9, 8.1 Hz, 1H), 7.15–7.35 (m, 6H).

Example 13

Ethyl ((3S*,4R*)-4-hydroxy-3-(phenylmethyl)-chroman-7-yl)acetic acid

Using the method of Example 4F with methanol as the solvent, methyl ethyl ((3S,4R)-4-hydroxy-3-(phenylmethyl)-chroman-7-yl)acetate (181 mg, 0.49 mmole) gave 57 mg (36%) of the acid as an oily solid. Treatment of this with an equivalent of sodium hydroxide in ethanol followed by concentration yielded 31 mg of the sodium salt as a light tan foam:

¹H NMR (CDCl₃) (free acid): 0.92 (t, J=7.3 Hz, 3H), 1.80 (m, 1H), 2.07 (m, 1H), 2.20 (m, 1H), 2.51 (dd, J=9.2, 13.7 Hz, 1H), 2.70 (dd, J=6.3, 13.7 Hz, 1H), 3.41 (t, J=7.6 Hz, 1H), 3.95 (dd, J=4.3, 11.2 Hz, 1H), 4.18 (dd, J=2.6, 11.2 Hz, 1 H), 4.47 (d, J=4.0 Hz), 6.84 (d, J=1.9 Hz, 1H), 6.9 (m, 1H), 7.15–7.35 (m, 6H).

Example 14

2-((3S*, 4R*)-4-Hydroxy-3-(2-thienylmethyl)chroman-7-yl-)-cyclopentanecarboxylic acid Using the method of Example 4F, the methyl ester of the title compound (610 mg, 1.55 mmole) gave after chromatography (5:20:75—HOAc: EtOAc:hexane) and recrystallization (cyclohexane—EtOAc) 367 mg (67%) of a white crystalline solid:

mp 145°–146° C., ¹H NMR (CDCl₃): 1.75 (m, 4H), 1.9 (m, 2H), 2.25 (m, 2H), 2.6 (m, 2H), 2.79 (dd, J=8.9, 14.9 Hz, 1H), 2.89 (dd, J=6.5, 14.9 Hz, 1H), 4.03 (dd, J=4.3, 11.2 Hz, 1H), 4.23 (dd, J=2.6, 11.2 Hz, 1H), 4.50 (d, J=4.0 Hz, 1H), 6.81 (d, J=3.4 Hz, 1H), 6.90 (d, J=1.9 Hz, 1H), 6.93 (dd, J=3.4, 5.1 Hz, 1H), 6.98 (dd, J=1.9, 8.0 Hz, 1 H), 7.15 (dd, J=1.2, 5.1 Hz, 1H), 7.26 (d, J=8.0 Hz, 1 H).

Example 15

((3S,4R)-4-Hydroxy-3-(phenylmethyl)-chroman-7-yl)-dimethylacetic acid

Using the same procedure as described in Example 4F, N-α-t-butoxycarbonyl-D-tryptophan ((3S, 4R)-3-benzyl-7-(1-carbomethoxy-1-methylethyl) chroman-4-yl) ester (786 mg, 1.25 mmole) yielded after chromatography (4:16:80—HOAc:EtOAc:hexane) and recrystallization (cyclohexane-EtOAc) 282 mg (69%) of white crystalline solid:

mp 141°–143° C.; [α]_D+32.3° ; ¹H NMR (CD₃CN): 1.50 (S, 6H), 2.15 (m, 1H), 2.45 (dd, J=9.1, 13.7 Hz, 1H), 2.71 (dd, J=6.2, 13.7 Hz, 1H), 3.90 (dd, J=4.9, 11.1 Hz, 1H), 4.12 (dd, J=2.7, 11.1 Hz, 1H), 4.37 (d, J=4.4 Hz, 1H), 6.79 (d, J=1.9 Hz, 1H), 6.93 (dd, J=1.9, 8.0 Hz, 1H), 7.15–7.35 (m, 6H).

Example 16

((3R, 4S)-4-Hydroxy-3-(phenylmethyl)-chroman-7-yl)-dimethylacetic acid

Using the same procedure as described in Example 4F, N-α-t-butoxycarbonyl-D-tryptophan ((3R, 4S)-3-benzyl-7-(1-carbomethoxy-1-methylethyl)chroman-4-yl) ester (191 mg, 0.56 mmole) yielded after chromatography (4:16:80—HOAc: EtOAc: hexane) and recrystallization (cyclohexane—EtOAc) 129 mg (70%) of white chunky crystals:

mp 143°–144° C.; [α]_D –33.8°; ¹H NMR (CDCl₃):1.57 (s, 6H), 2.2 (m, 1H), 2.52 (dd, J=9.2, 13.7 Hz, 1H), 2.71 (dd, J=6.3, 13.7 Hz, 1H), 3.95 (dd, J=3.6, 11.1 Hz, 1H), 4.19 (dd, J=2.7, 11.1 Hz, 1H), 4.48 (d, J=4.0 Hz, 1H), 6.91 (d, J=1.9 Hz, 1H), 6.98 (dd, J=1.9, 8.0 Hz, 1H), 7.15–7.35 (m, 6H).

Example 17

A- 3,3-(Spiro-2-phenylcyclopropyl-7-methoxy-2H-1-benzopyran-4-one

To a stirred slurry of trimethyloxosulfonium iodide (19.3g, 87.6 mmole) and NaH (60%, 3.67 g, 91.7 mmole) was added dimethylsulfoxide (140 ml) dropwise over 10 minutes. The mixture was stirred at room temperature for 1 hour then a solution of 3-phenylmethylene-7-methoxy-2H-1-benzopyran-4-one (11.1 g, 41.7 mmole) in 70 ml of dimethylsulfoxide was added dropwise over 5 minutes. The mixture was stirred for 4 hours and poured into 250 ml of 5% aqueous NH₄Cl. The mixture was extracted with 3×100 ml of ethyl acetate, washed with water and brine, then dried over MgSO₄. Filtration and solvent evaporation in vacuo gave a yellow oil which was passed through a short column of silica gel to give 11.2 g of a low melting yellow solid.

¹H-NMR (300 MHz, CDCl₃) 87.86 (1H, d, J=8.8 Hz), 7.21–7.39 (6H, m), 6.61 (1H, dd, J=8.8, 2.4 Hz), 6.36 (1H, d, J=2.4 Hz), 4.30 (1H, d, J=11.9 Hz), 3.92 (1H, d, J=11.9 Hz), 3.82 (3H, s), 3.01 (1H, dd, J=8.5, 1.6 Hz), 1.98 (1H, dd, 8.9, 4.8 Hz), 1.38 (1H, dd, J=8.5).

B. 3-Phenylethyl-7-methoxy-2H-1-benzopyran-4-one

A solution of the compound of step A (6.0 g) in acetic acid (100 ml) was hydrogenated over palladium/carbon catalyst in a Parr shaker flask at 60° C. under 55 psi of hydrogen for 20 hours. The solution was filtered through celite and the solvents removed. The crude solid was dissolved in 30 ml of acetic acid and 30 ml of HBr and refluxed for 18 hours. The mixture was cooled to room temperature, poured into 200 ml of ice-water and extracted with 3 times 75 ml of CHCl₃. The combined extracts were washed with water (3×) and brine, then dried and evaporated to give a blackish solid. Chromatography (silica gel 1:1 hexane:ether) gave 4.26 g pure title compound.

¹HNMR (300 MHz, CDCl₃): 7.81 (1H, d, J=8.9 Hz), 7.12–7.31 (5H, m), 6.55 (1H, dd, J=8.9 Hz, 2.4 Hz), 6.34 (1H, d, J=2.4 Hz), 5.89 (1H, s), 4.46 (1H, dd, J=11.4, 4.4 Hz), 4.26 (1H, dd, 11.4, 8.4 Hz), 2.69–2.83 (2H, m), 2.62 (1H, m), 2.22 (1H, m), 1.75 (1H, m).

Example 18

Trans-3,4-dihydro-4-hydroxy-3-(phenylmethyl)-7-(2-hydroxyethyl)-2H-benzopyran

To a stirred solution of 3-phenylmethylene-7-methoxycarbonylmethyl-2H-1-benzopyran-4-one (4.2 g, 14.3 mmole) in THF (70 ml) at 0° C. was added lithium aluminum hydride (2.16 g, 57.1 mmole) portionwise over 10 minutes. The mixture was slowly warmed to room temperature then heated at reflux for 5 hours. The mixture was cooled to 0° C. and 200 ml of saturated sodium-potassium tartrate solution was carefully added over 10 minutes. The mixture was stirred at room temperature overnight, the clear organic phase separated and the clear aqueous layer extracted with 2×100 ml of ether. The combined organic layers were washed with water and brine then dried over MgSO₄. Filtration followed by evaporation in vacuo and chromatography (silica gel 2:1→1:5 hexane:ether) gave 2.61 of the title compound (64% yield).

¹H-NMR (300 MHz, CDCl₃): 7.13–7.35 (6H, m), 6.82 (1H, dd, J=7.9, 0.6 Hz), 6.76 (1H, d, J=0.6 Hz), 4.49 (1H, t, brd), 4.23 (1H, dd, J=11.2, 2.6 Hz), 3.98 (1H, dd, J=11.2, 5.1

Hz), 3.87 (2H, m), 2.83 (2H, t), 2.70 (1H, dd, J=13.6, 7.2 Hz), 2.52 (1H, dd, J=13.6, 9.3 Hz), 2.14–2.26 (1H, m).

Example 19

A. Trans-3,4-dihydro-4-(t-butyldimethylsiloxy)-3-(phenylmethyl)-7-(2-hydroxyethyl)-2H-1-benzopyran Using the procedure of Example 5A, the compound of Example 18 (2.5 g, 8.7 mmole) was silylated with 2 equivalent of each reagent. The crude bis-silyl derivative (3.63 g) was dissolved in 35 ml of ethanol and (ppTs) added (356 mg, 1.4 mmole). The mixture was stirred at room temperature for 24 hours, the solvent evaporated in vacuo and the residue chromatographed (silica gel 3:1 hexane:ether) to afford the title compound (1.48 g).

$^1$H-NMR (300 MHz, CDCl$_3$): 7.09–7.32 (6H, m), 6.78 (1H, dd, J=7.9, 0.6 Hz), 6.74 (1H, d, J=0.6 Hz), 4.41 (1H, s, brd), 4.28 (1H, dd, J=10.8, 2.2 Hz), 3.98 (1H, dd, J=10.8, 1.6 Hz), 3.83–3.91 (2H, m), 2.82 (2H, m), 2.5 (2H, m), 2.05 (1H, m), 0.86 (9H, s), 0.02 (6H, s).

B. Trans-3,4-dihydro-4-(t-butyldimethylsiloxy)-3-(phenylmethyl)-7-[2-(3-ethoxycarbonylphenoxy)ethyl]-2H-1-benzopyran To a stirred solution of the compound of step A (720 mg, 18 mmole) in tetrahydrofuran (10 ml) was added diethylazodicarboxylate (430 μl, 2.5 mmole), triphenylphosphine (710 mg, 2.5 mmole) and ethyl 3-hydroxybenzoate (415 mg, 2.5 mmole). The mixture was refluxed for 3 days, the solvent removed in vacuo and the residue chromatographed (silica gel, 3:1 hexane:ether) to afford 258 mg of the title compound.

$^1$H-NMR (300 MHz, CDCl$_3$): 7.63 (1H, d, J=7.7 Hz), 7.57 (1H, s), 7.07–7.38 (8H, m), 6.87 (1H, d, J=8.1 Hz), 6.82 (1H, s), 4.43 (1H, s), 4.32 (1H, d, brd), 4.23 (2H, m), 4.02 (1H, d, brd), 3,981 (3H, s), 3.09 (2H, t), 2.55 (2H, m), 2.07 (1H, m), 0.89 (9H, s), 0.06 (6H, s).

C. Trans-3,4-dihydro-4-hydroxy-3-phenylmethyl-7-[2(2-ethoxycarbonylphenoxy)ethyl-2H-1-benzopyran Using the procedure of Example 5D, the compound of step B (240 mg) was desilylated giving 160 mg of a yellow oil. The oil was submitted to the procedure of Example 2I using methanol as solvent to afford 141 mg of the title compound. The melting point is 158°–159° C. on recrystallization with methanol.

Example 20

A. 7-Carbomethoxy-benzopyran-4-one

To a stirred solution of 7-trifluoromethylsulfonyloxy-benzopyran-4-one (7.89 g, 26.6 mmole) in DMF (54 ml) was added methanol (21.6 ml), palladium acetate (110 mg, 0.533 mmole), DPPF (590 mg, 1,066 mmole) and triethylamine (7.477 ml, 53.3 mmole). Carbon monoxide gas was bubbled through the solution for 5 minutes, and the mixture was stirred at 50° C. for 3 hours under 1 atmosphere of CO. After cooling, the mixture was poured into 120 ml of 1M sulfuric acid and extracted with 2×75 ml of ethylacetate. The combined organic fractions were washed with brine, dried over MgSO$_4$, and filtered. Solvent evaporation in vacuo and chromatography (silica gel 1:1 hexane:ether) gave 5.19 g of the title compound (94% yield).

$^1$H-NMR (300 MHz, CDCl$_3$): 7.96 (1H, d, J=9.2 Hz), 7.60–7.65 (2H, m), 4.6 (2H, t, J=6.7 Hz), 2.88 (2H, t, J=6.7 Hz).

B. Using the procedure of Example ID with methanol as solvent, the compound of step A (6.41 g, 31.0 mmole) gave 6.44 g of 3-phenylmethylene-7-carbomethoxy-benzopyran-4-one as a white solid, M.P. ~180° C. (decomposition). $^1$H-NMR (300 MHz, CDCl$_3$): 8.06 (1H, d, J=8.1 Hz), 7.90 (1H, s, brd), 7.79 (1H, dd, J=8.1, 1.4 hz), 7.64 (1H, d, J=1.4 Hz), 7.298=–7.50 (5H, m), 5.38 (2H, s), 3.94 (3H, s).

C. Using the procedure of Example 2I with ethyl acetate as solvent, the compound of step B (6.44 g) was hydrogenated for 2 hours to afford 6.4 g 3-phenylmethyl-7-carbomethoxy -benzopyran-4-one.

$^1$H-NMR (300 MHz, CDCl$_3$): 7.96 (1H, dd, J=8.1, 0.6 Hz), 7.65–7.63 (2H, m), 7.16–7.35 (5H, m), 4.40 (1H, dd, J=11.6, 4.3 Hz), 4.20 (1H, dd, J=11.6, 8.7 Hz), 3.82 (3H, s), 3.28 (1H, dd, J=13.9, 4.5 Hz), 2.92–3.05 (1H, m), 2.72 (1H, dd, J=13.9, 10.3 Hz),

M.P. 98°–100° C.

D. Using the procedure of Example 2G in methanol, the compound of step C (0.85 g, 2.8 mmole) was reduced to give trans(3,4-dihydro-4-hydroxy)-3-phenylmethyl-7-carbomethoxy -2H-1-benzopyran (320 mg).

M.P. 143°–144° C.

E.
4-Hydroxy-3-(phenylmethyl)-7-carboxy-2H-1-benzopyran

Using the procedure of Example 2I and methanol as solvent, the compound of step D (288 mg, 0.96 mmole) was saponified to give the title compound (247 mg).

$^1$H-NMR (300 MHz, DMSOd$_6$): 7.40–7.51 (2H, m), 7.13–7.32 (6H, m), 5.58 (1H, d, brd), 4.37 (1H, t, brd), 4.15 (1H, dd, J=11.3, 2.5 Hz), 3.90 (1H, dd, J=11.3, 5.2 Hz), 3.40–3.55 (1H, m), 3.30 (1H, m), 2.78 (1H, dd, J=13.7, 6.5 hz), 2.45 (1H, dd, J=13.7, 9.0 Hz), 2.09–2.19 91H, m).

Example 21

3-Diphenylmethyl-7- [(trifluoromethane sulfonyl)oxylbenzopyran-4-one

To a slurry of copper iodide (2.2 g, 11.6 mmole) in THF (20 ml) was added dimethyl sulfide (20 ml). The homogeneous solution was cooled to 0° C. and phenyl magnesium bromide was added dropwise over 5 minutes (7.7 ml, 3M in diethyl ether). After stirring at 0° C. for 20 minutes, the mixture was cooled to –30° C. and 3 -phenylmethylene-7-[(trifluoromethane sulfonyl)oxy]-benzopyran-4-one (3.0 g, 7.8 mmole) in 25 ml of THF was added over 10 minutes. The mixture was allowed to warm to 0 ° C. over 1 hour then poured into ice-cold saturated ammonium chloride. The mixture was extracted with 3×50 ml of ether, washed with brine, dried and evaporated in vacuo. Chromatography (silica gel 2:1 hexane:ether) gave 750 mg of the title compound.

$^1$H-NMR (300 MHz, CDCl$_3$): 7.89 (1H, d, J=8.7 Hz), 7.2014 7.42 (10 H, m), 7.00 (1H, d, J=2.3 Hz), 6.94 (dd, J=8.7, 2.3 Hz), 4.55 (1H, d, J=10.2), 4.46 (1H, dd, J=11.9, 3.4 Hz), 4.29 (1H, dd, J=11.9, 5.7 Hz), 3.53–3.63 (1H, m).

Example 22

A. 4-Hydroxy-2H-1-benzopyran-7-acetic acid methyl ester

Chromanone-7-acetic acid (10.26 g) was esterified using diazomethane in ethyl acetate and the crude reduced using the procedure of Example 2G to give a 76% yield (8.2 g) of the title compound.

$^1$H-NMR (300 MHz, CDCl$_3$): 7.22 (1H, d, J=9.2 Hz), 6.79 (1H, dd, J=9.2, 0.6 Hz), 6.71 (1H, d, J=0.6 Hz), 4.72 (1H, t, brd), 4.18–4.27 (2H, m), 3.68 (3H, s), 3.55 (2H, s), 2.99–2.18 (2H, m).

B. 3, 4-Dehydro-benzopyran-7-acetic acid methyl ester

To a stirred solution of the compound of step A (2.26 g, 10.23 mmole) in methylene chloride (30 ml) at −78° C. was added triethylamine (3.73 ml, 26.5 mmole), and DMAP (25 mg, catalytic) followed by the dropwise addition over 5 minutes of triflic anhydride neat (2.1 ml, 12.27 mmole). The yellow solution was stirred at −78° C. for 30 minutes then warmed to room temperature over 1 hour and poured into saturated NH$_4$Cl solution. The mixture was extracted with 2×50 ml of methylene chloride, the combined extracts washed with brine and dried over MgSO$_4$. The slurry was filtered and evaporated in vacuo to afford a yellow oil. Chromatography (silica gel, 1:1 hexane:ether) gave 860 mg (43% yield) of the title compound.

$^1$H-NMR (300 MHz, CDCl$_3$): 6.89 (1H, d, J=9.2Hz), 6.73 (dd, J=9.2, 0.6 Hz), 6.18 (1H, d, J=0.6 Hz), 6.39 (1H, d, J=11.1 Hz), 5.72 (1H, dt, J=11.1, 2.1 Hz), 4.75–4.80 (2H, m), 3.68 (3H, s), 3.63 (1H, s).

C. Trans-4-hydroxy-3 -phenyl-2-H-1-benzopyran-7-acetic acid methyl ester

To a stirred solution of the compound of step B (404 mg, 2.0 mmole) in 50% aqueous acetone (20 ml) was added palladium acetate (448 mg, 2.0 mmole), lithium chloride (255 mg, 6.0 mmole) and sodium acetate −3H$_2$O (1.08 g, 8.0 mmole). The mixture was stirred for 15 minutes then phenyl mercuric chloride (0.626 g, 2.0 mmole) was added and the mixture stirred for 6 hours. The black slurry was filtered through celite and washed with chloroform. The aqueous layer was extracted with 2×25 ml of chloroform, the combined organic layer washed with brine, dried over MgSO$_4$ and filtered. Solvent removal in vacuo and chromatography (silica gel—4:1 ether:hexane) gave 60 mg of the cis isomer eluting first and 230 mg of the trans isomer (39% yield).

M.P.=112°–113° C. $^1$H-NMR (300 MHz, CDCl$_3$): 7.15–7.43 (6H, m), 6.88 (1H, d, J=9.2 Hz), 6.8 (1H, s), 4.91 (1H, d, J=7.1 Hz), 4.14–4.39 (2H, m), 3.69 (3H, s), 3.58 (2H, s), 3.05–3.18 (1H, m ), 2.4 (1H, s, brd).

Example 23

Trans-3,4-dihydro-4-hydroxy-3-(phenylmethyl)-2H-1 -benzopyran-7-propionic acid A. To a stirred solution of 3-phenylmethyl-2H-1 -benzopyran-4-one-7-triflate (0.352 g, 0.911 mmole) in 3.3 ml of dry toluene was added allyl palladium chloride dimer (11 mg, 0.036 mmole), tri-o-tolylphosphine (40.4 mg, 0.144 mmole) and 1,1-ethoxysiloxycyclopropane (0.19 1 g, 1.1 mmole). Nitrogen was bubbled through the solution for 5 minutes, then the pressure tube sealed and the mixture heated at 140° C. After 1 hour the black mixture was cooled to room temperature, filtered through celite and the pad washed with CH$_2$Cl$_2$. Solvent removal in vacuo and chromatography (silica gel 5:1→1:1 hexane:ether gradient) gave 0.258 g (83% yield) of 3 -phenylmethyl-2H-1-benzopyran-4-one-7-propionic acid methyl ester.

$^1$H-NMR (300 MHz, CDCl$_3$): 7.84 (1H, d, J=7.9 Hz), 7.16–7.34 (5H, m), 6.86 (1H, dd, J=7.9, 0.6 Hz), 6.86 (1H, dd, J=7.9, 0.6 Hz), 6.79 (1H, d, J=0.6 Hz), 4.35 (1H, dd, J=4.3, 11.5 Hz), 4.1–4.23 (3H, m), 3.29 (1H, dd, J=4.3, 13.8 Hz), 2.82–2.99 (3H, m), 2.60–2.78 (3H, m), 1.26 (3H, t).

B. Using the procedure of Example 2G with methanol as solvent at room temperature, the compound of step A (700 mg, 2.16 mmole) was reduced and the trans isomer 4-hydroxy-3 -phenylmethyl-2H-1-benzopyran-7-propionic acid methyl ester saponified using the procedure of Example 2I to give the title compound (210 mg), 30% yield.

M.P.=161°–162° C.

Example 24

In accordance with Example 2I, the following acids were obtained by hydrolysis from their corresponding esters. The NMR data were measured at 300 MHz in CDCl$_3$, unless otherwise indicated.

| R$^1$ | R$^3$ | A | PRODUCT |
|---|---|---|---|
| Cyclopentyl carboxylic acid | 4-phenyl- phenylethyl | 0 | M.P. 202–203 |
| Cyclopentyl carboxylic acid | 3-phenyl- propyl | 0 | 7.18–7.59(6H, m), 6.71–6.80(2H, m), 4.51(1H, d, J=2.6Hz), 3.85–4.01(2H, m), 2.60–2.71(2H, m), 2.24–2.39(2H, m), 1.55–1.98(10H, m) |
| Cyclopentyl carboxylic acid | 3-phenyl- propyl | 0 | (trans) 7.12–7.30(6H, m), 6.92(1H, d, J=7.8Hz), 6.80(1H, s), 4.42(1H, d, J=4.6Hz), 4.26(1H, dd, J=11.1, 4.8Hz), 4.02(1H, dd, J=11.1, 7.4 Hz), 2.58–2.66(4H, m) 1.70–1.98) (10H, m) |
| * Cyclopent-yl-carboxylic acid | 4-phenyl- phenylmethyl | 0 | (3R, 4S) m.p. 167–168 [α]$_D^{22}$=−22±1 |
| * Cyclopent-yl-carboxylic acid | 4-phenyl- phenylmethyl | 0 | (3S, 4R) m.p. 167–168 [α]$_D^{22}$=+22±1 |
| Cyclopentyl carboxylic acid | 2,4-difluoro- phenylmethyl | 0 | m.p. 154–155 |
| Cyclopentyl carboxylic acid | 3-carboxy- phenylmethyl | 0 | m.p. 176–178 (dec.) 12.47(1H, bs), 7.74–7.85(2H, m), 7.40–7.49(2H, m), 7.28(1H, d, J=8.0Hz), 6.90(1H, dd, J=8.0, 1.8 Hz), 6.72(1H, d, J=1.8 Hz), 5.48(1H, bs), 4.32(1H, bs), 4.11(1H, dd, J=11.2, 2.4Hz), 3.88(1H, dd, J=11.2, |

-continued

Structure: benzene ring with OH on a CH, R³ on adjacent C, R¹ on ring, linker A

| R¹ | R³ | A | PRODUCT |
|---|---|---|---|
| | | | 5.7Hz), 3.39(1H, bs), 2.75–2.88(1H, m), 2.46(1H, m), 2.04–2.18 (1H, m), 1.55–1.88(8H, m) (in DMSOd₆) |
| Cyclobutyl carboxylic acid | phenylmethyl | 0 | (cis) m.p. 141–142 |
| Cyclobutyl carboxylic acid | phenylmethyl | 0 | (trans) m.p. 136–137 |
| Cyclopentyl carboxylic acid | phenylethyl | 0 | (cis) m.p. 152–154 |
| Cyclopentyl carboxylic acid | phenylethyl | 0 | (trans) m.p. 137–140 |
| Cyclopentyl carboxylic acid | bis-phenylmethyl | 0 | (cis) 7.13–7.41(10H m), 7.08(1H, d, J=7.9Hz), 6.88–6.91(1H, m), 4.41(1H, bs), 3.92–4.15 (3H, m), 2.82–2.96(1H, m), 2.52–2.61(2H, m), 1.65–1.92(6H, m) |
| Cyclopentyl carboxylic acid | bis-phenylmethyl | 0 | (trans) m.p. 208–210 |
| Cyclopentyl carboxylic acid | phenylmethyl | covalent bond | (cis) m.p. 145–146 |
| Cyclopentyl carboxylic acid | phenylmethyl | covalent bond | (trans) m.p. 141–142 |
| Cyclopentyl carboxylic acid | phenylmethyl | $CH_2$ | (cis) 7.18–7.36(7H, m), 7.11(1H, s, brd), 4.48(1H, d, J=3.7Hz), 2.58–2.98(5H, m), 1.54–1.90(10H, m) |
| Cyclopentyl carboxylic acid | phenylmethyl | $CH_2$ | (trans) m.p. 101–103 |
| 2-(3-car-bethoxy-phenoxy)-ethyl | phenylmethyl | 0 | (trans) m.p. 173–175 |
| Dimethyl carboxylic acid | cyclohexyl methyl | 0 | (cis) 7.20(1H, d, J=8Hz), 6.99(1H, dd, J=8.0, 1.7 Hz), 6.85(1H, d, J=1.7Hz), 4.55(1H, d, J=2.8Hz), 3.90–4.04(2H, m), 2.04–2.15(1H, m), 1.60–1.78(4H, m), 1.35–1.49(2H, m), 1.10–1.36(5H, m), 0.82–1.00(2H, m). |
| Dimethyl carboxylic acid | cyclohexyl methyl | 0 | (trans) 7.25(1H, d, J=8.0), 6.91(1H, dd, J=8.0, 1.7Hz), 6.82(1H, d, J=1.7Hz), 4.36(1H, d, J=4.2 Hz), 4.22(1H, dd, J=11.1, 2.6Hz), 3.97 (1H, dd, J=11.1, 4.6Hz), 1.98(1H, m), 1.60–1.79 (4H, m), 1.11–1.40(7H, m), 1.79–1.98(2H, m). |

* From the corresponding 4-t-butoxycarbonyl-D-tryptophan

Example 25

A. Methyl (3-hydroxyphenyl) acetate

Using the procedure of Example 2A with methanol as the solvent, (3-hydroxyphenyl) acetic acid (25.0 g, 164 mmole) gave 27.8 g (100%) of an oil:

¹H-NMR (CDCl₃): 3.57 (s, 2H), 3.69 (s, 3H), 5.26 (s, 1H), 6.2–6.3 (m, 2H), 6.82 (d, J=7.9 Hz, 1H), 7.18 (t, J=7.9 Hz, 1H).

B. Methyl (3-((1,1-dimethylethyl)dimethylsilyloxy)phenyl)acetate

Using the same procedure as described in Example 5A, the compound of step A (10.0 g, 60.2 mmole) yielded 16.0 g (95%) of the silyl ether as an oil:

¹H-NMR (CDCl₃): 0.17 (s, 6H), 0.94 (s, 9H), 3.54 (s, 2H), 3.66 (s, 3H), 6.6–6.7 (m, 2H), 6.80 (d, J=8 Hz, 1H), 7.10 (t, J=8 Hz, 1H).

C. Methyl diethyl-2-(3-((1,1-dimethylethyl) dimethylsilyloxy)phenyl)acetate

To a mixture of the compound of step B (5.00 g, 17.9 mmole) and ethyl iodide (6.96 g, 44.6 mmole) in dimethyl sulfoxide (180 ml) was added sodium hydride (2.143 g, 60% in oil, 53.6 mmole). After stirring at room temperature for 48 hours the mixture was carefully quenched with saturated ammonium chloride solution and extracted with EtOAc (2×). The extract was dried, filtered and concentrated to an oil which was chromatographed (5: 95—EtOAc: hexane) to give 1.045 g (17%) of the title compound as an oil:

¹H-NMR (CDCl₃): 0.17 (s, 6H), 0.71 (t, J=7.4 Hz, 6H), 0.96 (s, 9H), 2.00 (m, 4H), 3.62 (s, 3H), 6.7 (m, 1H), 6.8 (m, 1H), 7.0 (m, 1H), 7.15 (m, 1H); and 2,011 g (51%) of methyl diethyl(3-hydroxy)phenyl acetate as an oil:

¹H-NMR (CDCl₃): 0.71 (t, J=7.4 Hz, 6H), 2.0 (m, 4H), 3.63 (s, 3H), 5.67 (br s, 1H), 6.7–6.75 (m, 2H), 6.8 (m, 1H), 7.16 (t, J=7.8 Hz, 1H).

D. Methyl diethyl((3-hydroxy)phenyl)acetate

Using the same procedure as in Example 5D, the title compound of step C (1.00 g, 2.97 mmole) gave 411 mg (62%) of the phenol as an oil which was identical by NMR to that isolated as a by-product in step C.

E. Methyl diethyl(3-(2-propyn-1-yl)oxy)phenyl)acetate

The compound of step D (1.61 g, 7.20 mmole), propargyl bromide (1.2 g, 10 mmole) and potassium carbonate (1.59 g, 11.5 mmole) were vigorously stirred at room temperature for 48 hours. The reaction mixture was concentrated and the residue taken up in saturated NH₄Cl solution and ether. The ether layer was separated, dried, filtered and concentrated to an oil. This oil was chromatographed (10:90—EtOAc:hexane) to give 1.39 g (74%) of the desired propargyl ether as an oil:

¹H-NMR (CDCl₃):0.71 (t, J=7.4 Hz, 6H), 1.9–2.1 (m, 4H), 2.51 (t, J=2.4 Hz, 1H), 3.63 (s, 3H), 4.67 (d, J=2.4 Hz, 2H), 6.8–6.9 (m, 3H), 7.2–7.3 (m, 1H).

F. Methyl ((3-(3-chloro-2-propyn-1-yl)oxy)phenyl)diethylacetate

The compound of step E (1.89 g, 7.27 mmole) in THF (40 ml) at −25° C. was treated with lithium diisopropyl amide (5.33 ml, 1.5M in hexane, 8.0 mmole). After 40 minutes p-toluene sulfonyl chloride (1.52 g, 8.0 mmole) was added in small portions and then the mixture was stirred at −25° C. for 4 hours. While still cold, the reaction was quenched with saturated NH$_4$Cl solution and allowed to warm to room temperature. The mixture was extracted with ether and the separated ether layer washed with water, dried, filtered and concentrated to an oil. This oil was chromatographed (10:90—EtOAc:hexane) to give 1.33 g (62%) of the title compound as an oil:

$^1$H-NMR (CDCl$_3$): 0.71 (t, J=7.4 Hz, 6H), 1.9–2.1 (m, 4H), 3.64 (s, 3H), 4.67 (s, 2H), 6.8–6.9 (m, 3H), 7.2–7.3 (m, 1H).

G. Methyl (4-chromanon-7-yl) diethylacetate

The compound of step F (1.33 g, 4.5 mmole) was added to preheated (220° C.) diethylene glycol and heating continued for 5 hours. The cooled mixture was diluted with water and extracted with EtOAc. The extract was dried, filtered and concentrated to an oil. This oil was chromatographed (10:90—EtOAc:hexane) to give 557 mg (45%) of chromanone as an oil:

$^1$H-NMR (CDCl$_3$):0.72 (t, J=7.4 Hz, 6H), 1.9–2.15 (m, 4H), 2.78 (t, J=6.4 Hz, 2H), 3.65 (s, 3H), 4.53 (t, J=6.4 Hz, 2H), 6.85–6.9 (m, 3H), 8.1 (d, J=8.1 Hz, 1H).

H. Methyl diethyl (3-phenylmethylene-4-chromanon-7-yl) acetate

Using the procedure of Example 1D, the compound of step G (557 mg, 2.0 mmole), benzaldehyde (257 mg, 2.4 mmole) and pyrrolidine (223 mg, 2.4 mmole) in methanol gave after chromatography (5:95—EtOAc:hexane) 320 mg (37%) of the condensation product as a light yellow oil:

$^1$H-NMR (CDCl$_3$) :0.73 (t, J=7.4 Hz, 6H), 1.9–2.1 (m, 4H), 3.66 (s, 3H), 5.34 (d, J=1.8 Hz, 2H), 6.86 (d, J=1.7 Hz, 1H), 6.94 (dd, J=1.7, 8.3 Hz, 1H), 7.3–7.5 (m, 5H), 7.86 (br s (t?), 1H), 7.95 (d, J=8.3 Hz, 1H).

I. Methyl diethyl (3-phenylmethyl-4-chromanon-7-yl) acetate

Using the procedure of Example IE with ethanol as the solvent, the compound of step H (860 mg, 2.36 mmole) gave after chromatography (10:90—EtOAc:hexane) 431 mg (50%) of the reduced compound as an oil:

$^1$H-NMR (CDCl$_3$): 0.72 (2t, 6H), 1.9–2.1 (m, 4H), 2.71 (dd, J=10.4, 13.8 Hz, 1H), 2.85–2.95 (m, 1H), 3.26 (dd, J=4.3, 13.8 Hz, 1H), 3.65 (s, 3H) 4.16 (dd, J=8.4, 11.5 Hz, 1H), 4.35 (dd, J=4.4, 11.5 Hz, 1H), 6.85 (d, J=1.8 Hz, 1H), 6.90 (dd, J=1.8, 8.3 Hz, 1H), 7.2–7.4 (m, 5H), 7.84 (d, J=8.3 Hz, 1H).

J. Methyl diethyl((3R*,4S*)-3-phenylmethyl-4-hydroxychroman-7-yl)acetate

Using the procedure of Example 2G with methanol as the solvent, the compound of step I (381 mg, 1.04 mmole) and sodium borohydride (39 mg, 1.0 mmole) gave after chromatography (10:90–EtOAc:hexane) 180 mg (47%) of methyl diethyl ((3R*, 4R*) -3-phenylmethyl-4-hydroxychroman-7-yl)acetate as an oil:

$^1$H-NMR (CDCl$_3$): 0.70 (2t, 6H), 1.9–2.1 (m, 4H), 2.3 (m, 1H), 2.67 (dd, J=7.1, 13.7 Hz, 1H), 2.86 (dd, J =8.6, 13.6 Hz, 1H), 3.62 (s, 3H), 4.05–4.1 (m, 2H), 4.47 (br t, 1H), 6.7–6.8 (m, 2H), 7.1–7.4 (m, 6H); and 147 mg (38%) of the title compound as an oil:

$^1$H-NMR (CDCl$_3$): 0.72 (t, J=7.2 Hz, 6H), 1.9–2.1 (m, 4H), 2.2 (m, 1H), 2.53 (dd, J=9.3, 13.8 Hz, 1H), 2.72 (dd, J=6.1, 13.8 Hz, 1H), 3.65 (s, 3H), 3.95 (dd, J=4.3, 11.2 Hz, 1H), 4.18 (dd, J =2.7, 11.2 Hz, 1H), 4.48 (br t, 1H), 6.76 (d, J=1.9 Hz, 1H), 6.82 (dd, J=1.9, 8.0 Hz, 1H), 7.15–7.35 (m, 6H).

K. Diethyl((3R*, 4S*)-3-phenylmethyl-4-hydroxychroman-7-yl)acetic acid

Using the procedure of Example 2I with methanol as the solvent, the title compound of step J (140 mg, 0.38 mmole) gave after chromatography (5:10:85—HOAc:EtOAc:hexane) 83 mg (62%) of a white crystalline solid:

m.p. 67°–69° C.; $^1$H-NMR (CDCl$_3$): 0.75 (2t, 6H), 1.9–2.1 (m, 4H), 2.2 (m, 1H), 2.51 (dd, J=9.3, 13.8 Hz, 1H), 2.72 (dd, J=6.1, 13.8 Hz, 1H), 3.95 (dd, J =4.3, 11.2 Hz, 1H), 4.20 (d, J=2.7, 11.2 Hz, 1H), 4.49 (d, J =4.0 Hz, 1H), 6.83 (d, J =1.9 Hz, 1H), 6.89 (dd, J =1.9, 8.0 Hz, 1H), 7.15–7.35 (m, 6H).

Example 26

((3R*, 4S*) -4-Hydroxy-3-(phenylmethyl)-chroman-7-yl)acetylmethylamine

A mixture of ((3R*,4S*)-4-hydroxy-3-(phenylmethyl)-chroman-7-yl) acetic acid (320 mg, 1.07 mmole) and N-methylmorpholine (0.12 ml, 1.07 mmole) in THF (5 ml) was added to a cold (−20° C.) solution of isobutylchloroformate (0.14 ml, 1.07 mmole) in THF (5 ml). After 10 minutes more at −20° C., methylamine gas was bubbled through the solution for 5 minutes and the mixture was then allowed to warm to room temperature and stir for 90 minutes. The mixture was concentrated and the residue taken up in EtOAc. The resulting solution was washed with 1N HCl and saturated NaHCO$_3$ solution, dried, filtered and concentrated to a white solid. This was recrystallized (cyclohexane/EtOAc) to give 124 mg (37%) of the title compound as a white crystalline solid:

m.p. 183°–185° C.; $^1$H-NMR (CDCl$_3$): 2.05 (m, 1H), 2.31 (dd, J=9.4, 13.7 Hz, 1H) 2.56/2.57 (2s, 3H), 2.60 (dd, J =6.3, 13.7 Hz, 1H), 3.30 (s, 2H), 3.74 (dd, J=4.8, 11.1 Hz, 1H), 4.05 (dd, J=2.4, 11.1 Hz, 1H), 4.2–4.3 (m, 2H), 6.08 (br s, 1H), 6.58 (br s, 1H), 6.67 (dd, J=1.6, 7.6 Hz, 1H), 6.9–7.2 (m, 6H).

Example 27

((3R*, 4S*)-4-Hydroxy-3-(phenylmethyl)-chroman-7-yl)dimethylacetyl-methylamine A mixture of ((3R*,4S*)-4-hydroxy-3-(phenylmethyl)-chroman-7-yl) dimethylacetic acid (202 mg, 0.62 mmole), 1- (3-dimethylaminopropyl) -3-ethylcarbodiimide hydrochloride (130 mg, 0.68 mmole), methylamine (0.62 ml, 1.0 M in THF, 0.62 mmole) in CH$_2$Cl$_2$ (5 ml) was stirred at room temperature for 16 hours. The mixture was then washed with water (2×), dried, filtered and concentrated to an oil which was chromatographed (25:75—hexane:EtOAc) yielding 141 mg (67%) of a glass:

¹H-NMR (CDCl₃): 1.54/1.55 (2s, 6H), 2.2 (m, 1H), 2.55 (dd, J=9.3, 13.7 Hz, 1H), 2.71/2.73 (2s, 3H), 2.72 (dd, 1H) (largely obscured by the CH₃N peak), 3.96 (dd, J=7.3, 11.2 Hz, 1H), 4.20 (dd, J=2.6, 11.2 Hz, 1H), 4.51 (br t, 1H), 5.29 (br, s, 1H), 6.88 (d, J=1.9 Hz, 1H), 6.94 (dd, J=1.9, 8.0 Hz, 1H), 7.15–7.35 (m, 6H).

Example 28

((3R*,4S*)-4-Hydroxy-3-(phenylmethyl-chroman-7-yl)acetylpyrrolidine

Using the same procedure as in Example 27 ((3R*,4S*)-4-hydroxy-3- (phenylmethyl) -chroman-7-yl) acetic acid (490 mg, 1.5 mmole), 1- (3-dimethylaminopropyl) -3-ethylcarbodiimide hydrochloride (345 mg, 1.8 mmole) and pyrrolidine (117 mg, 1.65 mmole) gave after chromatography (50:50—hexane:EtOAc) 172 mg (30%) of a foam:

¹H-NMR (CDCl₃): 1.50 (s, 6H), 1.5–1.7 (m, 4H), 2.2 (m, 1H), 2.55 (dd, J=9.1, 13.7 Hz), 2.7–2.85 (m, 3H), 3.49 (br t, 2H), 3.96 (dd, J=7.3, 11.2 Hz, 1H), 4.20 (dd, J=2.6, 11.2 Hz, 1H), 4.49 (br t, 1H), 6.77 (br s, 1H) 6.80 (br d, J=7.9 Hz, 1H), 7.15–7.35 (m, 6H).

Example 29

((3R*, 4S*)-4-Hydroxy-3-(phenylmethyl)-chroman-7-yl) dimethylacetyl(4-hydroxy-1 -butyl)amine Using the procedure of Example 27, ((3R*,4S*)-4 -hydroxy-3- (phenylmethyl) chroman-7-yl) dimethylacetic acid (490 mg, 1.5 mmole), 1- (3-dimethylaminopropyl) -3-ethylcarbodiimide hydrochloride (345 mg, 1.8 mmole) and 4-hydroxy-1-butanol (147 mg, 1.65 mmole) gave after chromatography (15:85—hexane:EtOAc) 181 mg (30%) of a glass:

¹H-NMR (CDCl₃): 1.35–1.55 (m, 4H), 1.58 (s, 6H), 2.2 (m, 1H), 2.55 (dd, 1H), 2.73 (dd, 1H), 3.15–3.3 (m, 2H), 3.55 (m, 2H), 3.98 (dd, 1H), 4.23 (dd, 1H), 4.51 (br t, 1H), 5.35 (br s, 1H), 6.90 (d, 1H), 6.95 (dd, 1H), 7.15–7.35 (m, 6H).

Example 30

A. Ethyl 3-(((3R*,4S*)-4-hydroxy-3-(phenylmethyl)-chroman-7-yl)dimethylacetylamino)benzoate Using the procedure of Example 27, ((3R*,4S*)-4 -hydroxy-3-(phenylmethyl)chroman-7-yl)dimethylacetic acid (816 mg, 2.5 mmole), 1-(3-dimethylaminopropyl)-3-ethylcarbodiimide hydrochloride (575 mg, 3.0 mmole) and ethyl 3-(aminobenzoate (413 mg, 2.5 mmole) gave after chromatography (80:20—hexane:EtOAc) 372 mg (32%) of the title compound as an oil.

B. 3,(((3R*,4S*)-4-Hydroxy-3-(phenylmethyl)-chroman-7yl)dimethylacetylamino)benzoic acid In accordance with Example 2I, the title compound of step A (359 mg, 0.76 mmole) gave after chromatography (4:16:80—HOAc:ethylacetate:hexane) 149 mg (44%) of the acid as a white solid:

m.p. >200° C.; ¹H-NMR (d₆-Me₂SO): 1.55 (s, 6H), 2.1 (m, 1H), 2.42 (dd, 1H), 2.73 (dd, 1H), 3.9 (m, 1H), 4.08 (br d, 1H), 4.8 (br s, 1H), 5.45 (br s, 1H), 6.79 (br s, 1H), 6.90 (br d, 1H), 7.15–7.35 (m, 9H), 7.58 (d, 1H), 7.84 (d, 1H), 8.10 (s, 1H), 9.25 (s, 1H).

Example 31

The following compounds were prepared according to the method of the indicated Example. The melting points are in ° C. The NMR data were measured in CDCl₃, unless otherwise indicated, at 3 00 MHz.

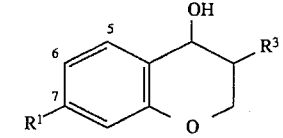

| R¹ | R³ | Example | Product |
|---|---|---|---|
| 2-propionic acid | phenyl methyl | 2I | (trans) 1.47(d, 7), 2.18(m), 2.53(dd, 12, 9), 2.72(dd, 12, 6), 3.70(9, 7), 3.96(dd, 10, 4), 4.19(d, 10), 4.48 (d, 3), 6.84(s), 6.91(d, 8), 7.1–7.5(m). |
| 2-propionic acid | phenyl methyl | 2I | (cis) 1.47(d, 7), 2.30 (m), 2.66(dd, 12, 7), 2.86(dd, 12, 8), 3.65(9, 7), 4.07(d, 7), 4.48 (d, 3), 6.79(s), 6.81(d, 8), 7.13(d, 8), 7.17–7.26(m). |
| 2-propionic acid (at position 6) | phenyl methyl | 2I | (cis) m.p. 129–131 |
| 2-propionic acid (at position 6) | phenyl methyl | 2I | (trans) m.p. 160–162 |
| 2-propionic acid (sodium salt) | 2-pyridylmethyl | 2I | (cis) m.p. 180–185 |
| 2-propionic acid (sodium salt) | 2-pyridylmethyl | 2I | (trans) m.p. 200–205 |
| 2-propionic acid | 2-pyridylmethyl | 2I | (trans racemic, 3S, 4R) 1.31(d, 7), 2.33 (m), 2.59(dd, 13, 7), 2.81(dd, 13.6), 3.57(d, 7), 3.89(dd, 12, 6), 4.13 (dd, 12, 2), 4.29(d, 5), 6.65(s), 6.79(d, 8), 7.15–7.4(m), 7.68 dd, 8, 8), 8.47(d, 5), (d₆-DMSO) |
| 2-propionic acid | 2-pyridylmethyl | 2I | (trans racemic, 3R, 4S) 1.31(d, 7), 2.33(m), 2.58(dd, 13, 7), 2.81 (dd, 13, 6), 3.57(d, 7), 3.89(dd, 10, 5), 4.12(d, 12), 4.29(d, 5), 6.65(s), 6.79(d, 8), 7.15–7.4(m), 7.68(dd, 8, 8), 8.47(d, 5), (d₆-DMSO) |
| acetic acid | phenylmethyl | 2I | (trans) m.p. 170–171 |
| acetic acid | phenylmethyl | 2I | (trans, one enantiomer) m.p. 163–165 [α]_D^{23}= -38.94° (methanol) |
| acetic acid | phenylmethyl | 2I | (cis, one enantiomer) m.p. 163–165 [α]_D^{23}= +38.94° (methanol) |
| 2-propionic acid | m-methoxy-phenylmethyl | 2I | (trans) IR(CHCl₃): 3667, 3587, 3506, 3000(b), 1714, 1619, 1602, 1578 |
| 2-propionic acid | m-methoxy-phenylmethyl | 2I | (cis) IR(CHCl₃): 3657, 3594, 3497, |

37
-continued

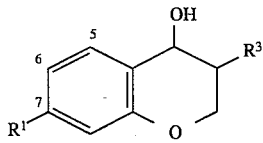

| R¹ | R³ | Example | Product |
|---|---|---|---|
| acetic acid methyl ester | m-methoxyphenylmethyl | 2I | 3000(b), 1712, 1618, 1601, 1578 (racemic) m.p. 126–127 |
| acetic acid, sodium salt | m-methoxyphenylmethyl | 2I | (cis, racemic) m.p. 244–245 |
| acetic acid, sodium salt | m-methoxyphenylmethyl | 2I | (trans, racemic) m.p. 214–216 |
| 2-methylpropionic acid | 2,4-difluorophenylmethyl | 2I | (trans, racemic) m.p. 128–129.5 |
| 2-methylpropionic acid | m-fluorophenylmethyl | 2I | (trans, racemic) m.p. 171–172.5 |
| 2-methylpropionic acid | 2,4-difluorophenylmethyl | 2I | (cis, racemic) m.p. 187–188.5 |
| 2-methylpropionic acid | m-fluorophenylmethyl | 2I | (cis, racemic) m.p. 169–169.5 |
| 2-methylpropionic acid | 3-pyridylmethyl | 2I | m.p. 188–190 |
| 2-methylpropionic acid | 2-pyridylmethyl | 2I | (cis) m.p. 149–150 |
| 2-methylpropionic acid | 2-pyridylmethyl | 2I | (trans, racemic) Calculated for $C_{19}H_{21}NO_4 \cdot \frac{1}{2}H_2O$: C, 67.85; H, Found: C, 68.23; H, 6.26 |
| 2-methylpropionic acid | m-trifluorophenylmethyl | 2I | (cis) 1.46(s), 2.02(m), 2.62(dd, 14.6), 2.86(dd, 14, 8), 3.98(m), 4.36(d, 4), 6.79(3), 6.81(d, 8), 7.06(d, 8), 7.3–7.5(m) |
| 2-methylpropionic acid | p-chlorophenylmethyl | 2G | (cis) m.p. 143–144.5 |
| 2-methylpropionic acid | p-chlorophenylmethyl | 2G | (trans) m.p. 128–129.5 |
| cyclopentyl carboxylic acid (5-fluoro) | phenylmethyl | 2I | (cis, racemic) m.p. 144–145 |
| cyclopentyl carboxylic acid (5-fluoro) | phenylmethyl | 2I | (trans, racemic) m.p. 185–187 |

Example 32

A mixture of 4.28 g (0.010 mol) of an enantiomeric mixture of 3,4-dihydro-4-hydroxy-3-(4-phenylbenzyl)-2H-1-benzopyran-7-cyclopentanecarboxylic acid and 0.826 g (0.005 mol) of (+)-ephedrine is dissolved in 150 ml of 3% aqueous ethyl acetate. The solution is stirred overnight (20 hours), the salt filtered under vacuum, rinsed with 2×10 ml ethyl acetate and air-dried. The salt is recrystallized from 3% aqueous ethyl acetate in a 30:1 volume (ml):mass (g) ratio until more than 95% pure as determined by optical rotation ($[\alpha]^{22}_D$>+6.7, c=1.0, MeOH). The salt is slurried in ethyl acetate and the pH is adjusted to 2 with dilute HCl. The mixture is stirred for one hour. The phases are separated and the organic phase is dried over MgSO$_4$, filtered and concentrated in vacuo. The crude acid is recrystallized from acetonitrile to yield 1.7 g (79%) of a white crystalline solid, m.p. 170°–172° C., which corresponds to the (3R, 4S) isomer. $[\alpha]^{22}_D$=−22.0(c=1.0, MeOH) Anal. calc'd. for $C_{28}H_{28}O_4$: C, 78.48; H, 6.59. Found: C, 78.51;, H, 6.47.

The above procedure utilizing (−)-ephedrine gives the (3S, 4R) isomer as a white crystalline solid, m.p. 169°–171° C. $[\alpha]^{22}_D$=−20.87(c=1.0, MeOH) Anal. calc'd. for $C_{28}H_{28}O_4$: C, 78.48; H, 6.59. Found: C, 78.51;, H, 6.53.

We claim:

1. A compound of the formula

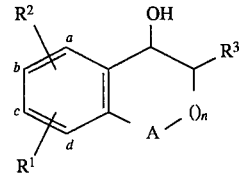

wherein

A is O;

n is 1;

$R^1$ is a substituent at position b or c as follows: carboxy, cis or trans —$(CH_2)_m$—$CR^4$=$CR^5$—$CO_2H$,

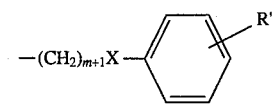

wherein m is 0, 1 or 2, R' is carboxy, or $CH_2OH$, and X is O, $CH_2$, S, NH or $N(C_1-C_6)$ alkyl; —$(CH_2)_m CR^4R^5R^6$ wherein m is as defined above, $R^4$ and $R^5$ are hydrogen or each independently are $C_1-C_6$ alkyl, or are taken together with the carbons to which they are attached to form $C_3-C_7$ cycloalkyl; and $R^6$ is hydroxyl, carboxy, or —$CONR^7R^8$ wherein $R^7$ and $R^8$ are hydrogen or each independently are $C_1-C_6$ alkyl, hydroxy substituted $C_1-C_6$ alkyl, $C_1-C_4$ perfluoroalkyl, $C_1-C_6$ alkylsulfinyl, phenylsulfinyl, $C_1-C_6$ alkylsulfonyl, phenylsulfonyl, $R^9$-substituted phenyl, or hydroxy, except that $R^7$ and $R^8$ cannot be both hydroxy;

$R^2$ is hydrogen or is one or any two of the following: fluoro, chloro, $C_1-C_6$ alkyl, $C_1-C_6$ alkoxy, $C_1-C_4$ perfluoroalkyl, $C_1-C_4$ perfluoroalkoxy, $C_1-C_6$ alkylthio, $C_1-C_6$ alkylsulfinyl or $C_1-C_6$ alkylsulfonyl;

$R^3$ is —$(CH_2)_q CHR^{11}R^{12}$, —$(CH_2)_q R^{12}$, —$O(CH_2)_p CHR^{11}R^{12}$, or —$O(CH_2)_p R^{12}$, wherein p is 0, 1 or 2 and q is 0, 1, 2, or 3;

$R^{11}$ is hydrogen, $C_1-C_6$ alkyl or $R^{16}$-substituted phenyl;

$R^{12}$ is $C_1-C_6$ alkyl or $C_3-C_8$ cycloalkyl; or phenyl, furyl, or naphthyl, each of which is optionally substituted by phenyl, $R^{15}$ or $R^{15}$-substituted phenyl wherein $R^{15}$ is as defined above; $R^9$, $R^{15}$, and $R^{16}$ are hydrogen or each independently is one or any two of the following: fluoro, chloro, $C_1-C_6$ alkyl, $C_1-C_6$ alkoxy, $C_1-C_4$ perfluoroalkyl, $C_1-C_4$ perfluoroalkoxy, $C_1-C_6$ alkylthio, $C_1-C_6$ alkylsulfinyl or $C_1-C_6$ alkylsulfonyl;

and the salts and esters of those compounds of formula I containing a carboxy group, wherein the esters contain ester groups selected from the group consisting of $C_1-C_6$ alkyl, phenyl($C_1-C_6$)alkyl, $C_3-C_7$ cycloalkyl, and phenyl and benzyl substituted by fluoro, chloro, $C_1-C_6$ alkyl or $C_1-C_6$ alkoxy.

2. A compound according to claim 1 wherein $R^3$ is benzyl, 4-fluorobenzyl, 4-phenylbenzyl, 4-(4-fluorophenyl)benzyl, phenethyl or phenoxy.

3. A compound according to claim 1 wherein $R^2$ is hydrogen or monofluoro.

4. A compound according to claim 1 wherein $R^1$ is at position c and is 1-carboxyethyl, 2-carboxy-2-propyl, 1-carboxypropyl, 3-carboxy-3-pentyl, 1-carboxycyclopentyl, or 1-carboxycyclohexyl.

5. A compound according to claim 2 wherein $R^3$ and the adjacent hydroxy group are trans.

6. A compound according to claim 5 wherein the absolute stereochemistry at the position to which $R^3$ is joined is S and the position to which the hydroxy group is joined is R and the optically pure salt thereof with L-ephedrine.

7. A compound according to claim 5 wherein the absolute stereochemistry at the position to which $R^3$ is joined is R and at the position to which the hydroxy group is joined is S and the optically pure salt thereof with D-ephedrine.

8. A compound according to claim 1 wherein A is O, $R^3$ is phenethyl, $R^2$ is hydrogen, $R^1$ is 1-carboxycyclopentyl at position c, and $R^3$ and the adjacent hydroxy group are cis.

9. A compound according to claim 1 wherein $R^1$ is carboxy; cis or trans —$(CH_2)_m$—$CR^4$=$CR^5$—$CO_2H$;

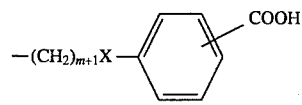

wherein m is 0, 1 or 2 and X is O, $CH_2$, S, NH or $N(C_1-C_6)$ alkyl; or —$(CH_2)_m CR^4 R^5 COOH$ wherein m is as defined above and $R^4$ and $R^5$ are hydrogen or each independently are $C_1-C_6$ alkyl or are taken together with the carbons to which they are attached to form $C_3-C_7$ cycloalkyl, in the form of the optically pure salt thereof with d-ephedrine.

10. A pharmaceutical composition for the treatment of $LTB_4$-induced illnesses which comprises a compound according to claim 1 and a pharmaceutically acceptable carrier.

* * * * *